US012389848B2

(12) United States Patent
Hirai et al.

(10) Patent No.: US 12,389,848 B2
(45) Date of Patent: Aug. 19, 2025

(54) STEVIA PLANT HAVING HIGH REBAUDIOSIDE M CONTENT RATIO AND SCREENING METHOD FOR SAME

(71) Applicant: SUNTORY HOLDINGS LIMITED, Osaka (JP)

(72) Inventors: Tadayoshi Hirai, Kyoto (JP); Kazunari Iwaki, Kanagawa (JP); Kentaro Ochiai, Kyoto (JP); Saori Takeyama, Kanagawa (JP); Katsuro Miyagawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 414 days.

(21) Appl. No.: 17/924,532

(22) PCT Filed: May 11, 2021

(86) PCT No.: PCT/JP2021/017954
§ 371 (c)(1),
(2) Date: Nov. 10, 2022

(87) PCT Pub. No.: WO2021/230257
PCT Pub. Date: Nov. 18, 2021

(65) Prior Publication Data

US 2023/0225273 A1 Jul. 20, 2023

(30) Foreign Application Priority Data

May 12, 2020 (JP) ................................ 2020-084129

(51) Int. Cl.
*A01H 6/14* (2018.01)
*A23L 27/30* (2016.01)
*A23L 33/105* (2016.01)
*C07H 15/256* (2006.01)
*C12Q 1/6895* (2018.01)

(52) U.S. Cl.
CPC ............ *A01H 6/1488* (2018.05); *A23L 27/36* (2016.08); *A23L 33/105* (2016.08); *C07H 15/256* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2007/0116835 A1 5/2007 Prakash et al.
2011/0183056 A1 7/2011 Morita et al.
2013/0202742 A1 8/2013 Prakash et al.
2014/0187761 A1 7/2014 Morita et al.
2016/0058050 A1 3/2016 Morita et al.
2017/0283819 A1* 10/2017 Markosyan ............ C07H 21/04
2018/0077959 A1 3/2018 Morita et al.
2019/0357581 A1 11/2019 Morita et al.
2020/0281141 A1 9/2020 Iwaki et al.
2021/0037864 A1 2/2021 Morita et al.
2021/0246517 A1 8/2021 Hirai et al.

FOREIGN PATENT DOCUMENTS

WO 2007/070224 A2 6/2007
WO 2010/038911 A1 4/2010
WO 2019/074089 A1 4/2019
WO 2020/027155 A1 2/2020

OTHER PUBLICATIONS

Herlache, “Novel Stevia Varieties with Superior Taste Profile for Sweeteners”, MSU Technologies, accessed at http://msut.technologypublisher.com/technology/22776 (Sep. 2, 2016).
International Search Report issued in PCT/JP2021/017954, dated Aug. 3, 2021, along with an English translation thereof.

* cited by examiner

*Primary Examiner* — Charles Logsdon
(74) *Attorney, Agent, or Firm* — GREENBLUM & BERNSTEIN, P.L.C.

(57) ABSTRACT

A method of screening for a stevia plant with high rebaudioside M content ratio, that includes detecting from a test stevia plant the presence and/or absence of at least one of (1) and (2), and at least one of (3) to (7): (1) homozygous for the allele wherein position 290 of SEQ ID NO: 1 is T; (2) homozygous for the allele wherein position 33 of SEQ ID NO: 2 is A; (3) homozygous for the allele wherein position 44 of SEQ ID NO: 3 is T; (4) homozygous for the allele wherein position 40 of SEQ ID NO: 4 is T; (5) homozygous for the allele wherein position 48 of SEQ ID NO: 5 is C; (6) homozygous for the allele wherein positions 55-72 of SEQ ID NO: 6 are deleted; (7) homozygous for the allele wherein position 50 of SEQ ID NO: 7 is A.

17 Claims, 2 Drawing Sheets

Specification includes a Sequence Listing.

FIG. 1

GGCAGCCATTGATGATGTTGTTGAATGTGATTAATTTGAATGTTATAAAGAAT
TTGGAAAAGAAAAAGGAGGGGACAAAGTTGATGAAATTAGGGGAGTTATGA
TTATGATGGCCATGGTGATTGTGATGAGTGGCACTATGTAATCTAATATTTGA
AGATATGAGACCACTTGACCATGTTATAATCTTATACAAAATAATTAATCCCTC
ACGGTAATTTTTTTCTAATCCTTAAACTGAAATTTGAAAGTAATTTGAGATAGT
GTTTCCCCTAATTTATGCTTTTAGTATGCATTTATTCTATCATATTTTCTATGAG
AATTGG (SEQ ID NO:1)

FIG. 2

TGATTTTGAAAGGATCTGACTGTATGTTTATAAGACATAGTTATGAGTTTGAA
CCCCAATGGCTAACCCT (SEQ ID NO:2)

FIG. 3

AAGGTTCTTTATTTTTAAACTTATGTTAATTTATTGTATCTTGTAGTTAATCAAG
AGATGCTCTCTTGGAGAAATTTTATGGTCATAAAACCTATATCAAAGAGATGC
TCTCTTGGTATATTCCATACTTAAAATATCTATTTTGGAAAAAAAGTGTAGCAT
CTTCCTGCTTTTAGTAGGTGTCAATCATTATTAAATTTCACAAAACCGTGCAA
GAATCCCAGTTTCCCTATAGTTTGTATACGTTCCTGATCTAGTATTTTACTTAT
GTTTCAAATCAATCCAATCATGCTTGTGTCCGAAAATTAAAAAACAAGGGTAT
TGGATGCCCTGTACCACTATTATTAACTTTTCAGAAAAACGTGTAGCATGTGT
ACATAAGG (SEQ ID NO:3)

FIG. 4

TAATCATCCAAACCCTAATCTCGCCAAACAACCGAATACTGATCCAAACCCT
GAAATGAGCACAACTCTTGAACCTGATCACGAGAATGAAGAGCACAAACAT
GTTATGACACATGTAAACGATGGTTTTTGCTACATGAAAACCCTAGAAGACG
AAACCCGTTTAACTGTAAATCTTGAAAACACATTCTTTGATGAAAAACCCCTT
TCGTATCCGGATCTTATGGACTTTTCTGCATCGAAAACGGACGAATACGACT
TCTATGATGAACTTGAAGAGCTGCCAATGTCTTCCTC (SEQ ID NO:4)

FIG. 5

CGATGGTTTTTGCTACATGAAAACCCTAGAAGACGAAACCCGTTTAACTGTA
AATCTTGAAAACACATTCTTTGATGAAAAACCCCTTTCGTATCCGGATCTTAT
GGACTTTTCTGCATCGAAAACGGACGAATACGACTTCTATGATGAACTTGAA
GAGCTGCCAATGTCTTCCTCATCATTCAAAAGCTTCATGAGAAGTAATTTCT
TTGAGGAAAGAGTTCTTGTTCAACCTTATTGATTAAGAATTTAAGGGAAGCA
GATTATATATGTAATTAAATTTTGGTATTTATACTTTGAACTTAATTAATAATTATA
ATAATAATCCCAACTAGAGGCACTTAGTGGAGATTACTTATATATAATACTAATT
CAAGGATTATTGCTGGT (SEQ ID NO:5)

FIG. 6

CGCAAACACGTATACTAATCACGTAACATATTTTTTATTTCTAAATTAAAATTTT
ATAACAATATCATACTTGAATTAAAGATAACATAATATTTATTTTTAGAGTGTAA
CTTCTAAAAAATATCAACCTACGAAAAAGTTGTACATACCATGCTAAA
(SEQ ID NO:6)

FIG. 7

ATACAAAAACACAACCCATATGGTCAAATCAACCCATTCATGAGTAATCAGG
TCAAATTCGCTATCTGAGCTGATGCATTCAACTATTTGGTCTCTTTTTAACAT
TTATTTTTTTTATTATTTTGAATGTAGAAACTTTGGAACTACTCAACTGGTAAG
TTCTTGAAGATGTATACCGGTCATGTAAACAAAACATATTGTATAACTCCGAC
TTTTTCTGTAACAAATGGAAAATATATTGTTAGTGGTTCAGAAGATCATTGTG
TCTACATATGGGATTTACAAGGG (SEQ ID NO:7)

STEVIA PLANT HAVING HIGH REBAUDIOSIDE M CONTENT RATIO AND SCREENING METHOD FOR SAME

TECHNICAL FIELD

The present invention relates to a stevia plant with high rebaudioside M content ratio, a screening method therefor, etc.

BACKGROUND ART

In response to consumers' diversified needs, various drinks have been developed and are commercially available. Saccharides such as sucrose are components very commonly blended in drinks for the purpose of, for example, conferring sweetness. However, their influence on health due to excessive consumption has been pointed out. Thus, there are growing needs for lower calorie and naturally derived sweeteners. For example, Patent Literature 1 discloses a functional sweetener composition containing a vitamin, a high intensity sweetener, and a sweetness improving composition.

Steviol glycoside is known as a sweet component contained in a stevia extract. The stevia extract is mainly extracted and purified from a stevia leaf. Stevia is a perennial plant of the family Asteraceae with Paraguay in the South America as its place of origin, and its scientific name is *Stevia rebaudiana* Bertoni. Stevia contains a component having approximately 300 or more times the sweetness of sugar and is therefore cultivated for use of this sweet component extracted therefrom as a natural sweetener. The presence of various glycosides such as rebaudioside A (hereinafter, "rebaudioside A" is also abbreviated as "Reb"), RebB, RebC, RebD, RebE and RebD has been reported as steviol glycoside (Patent Literature 2). Among various steviol glycosides, for example, RebA is evaluated as a high intensity sweetener having good quality of sweetness and is widely used. The other steviol glycosides have also been increasingly found to have their unique sweetness and associated taste.

Under these circumstances, a method for screening stevia plant with high RebM content is known (Patent Literature 3).

CITATION LIST

Patent Literature

Patent Literature 1: WO2007/070224
Patent Literature 2: WO2010/038911
Patent Literature 3: WO2019/074089

SUMMARY OF INVENTION

Technical Problem

RebM reportedly has good quality of taste, among steviol glycosides, but cannot be obtained in large amounts from natural stevia plants. Thus, the obtainment thereof is of concern.

Means for Solving the Problems

In one aspect, the present invention provides the following.

[1] A method of screening for a stevia plant with high rebaudioside M content ratio, comprising a step of detecting from the genome of a test stevia plant the presence and/or the absence of at least one of the following genetic features (1) and (2), and the presence and/or the absence of at least one of the following genetic features (3) to (7).

(1) Homozygous for the allele wherein the base at the position corresponding to position 290 of SEQ ID NO: 1 is T.
(2) Homozygous for the allele wherein the base at the position corresponding to position 33 of SEQ ID NO: 2 is A.
(3) Homozygous for the allele wherein the base at the position corresponding to position 44 of SEQ ID NO: 3 is T.
(4) Homozygous for the allele wherein the base at the position corresponding to position 40 of SEQ ID NO: 4 is T.
(5) Homozygous for the allele wherein the base at the position corresponding to position 48 of SEQ ID NO: 5 is C.
(6) Homozygous for the allele wherein the portion corresponding to positions 55-72 of SEQ ID NO: 6 is deleted.
(7) Homozygous for the allele wherein the base at the position corresponding to position 50 of SEQ ID NO: 7 is A.

[2] The method according to [1], further comprising a step of measuring the content of rebaudioside M in a test stevia plant tissue in which the presence and/or the absence of the genetic features has/have been detected.

[3] The method according to [1] or [2], wherein the rebaudioside M content ratio of the stevia plant with a high rebaudioside M content ratio is higher by 10% or more than that of a stevia plant selected by a screening method comprising a step of detecting the presence and/or the absence of at least one of the genetic features (3) to (7) but not comprising a step of detecting the presence and/or the absence of at least one of the genetic features (1) and (2).

[4] The method according to any one of [1] to [3], wherein the step of detecting the presence and/or the absence of the genetic features is performed by use of CAPS method, dCAPS method or TaqMan PCR method.

[5] A screening kit for a stevia plant with high rebaudioside M content ratio, comprising a reagent for detecting the presence and/or the absence of at least one of the following genetic features (1) and (2), and a reagent for detecting the presence and/or the absence of at least one of the following genetic features (3) to (7).

(1) Homozygous for the allele wherein the base at the position corresponding to position 290 of SEQ ID NO: 1 is T.
(2) Homozygous for the allele wherein the base at the position corresponding to position 33 of SEQ ID NO: 2 is A.
(3) Homozygous for the allele wherein the base at the position corresponding to position 44 of SEQ ID NO: 3 is T.
(4) Homozygous for the allele wherein the base at the position corresponding to position 40 of SEQ ID NO: 4 is T.
(5) Homozygous for the allele wherein the base at the position corresponding to position 48 of SEQ ID NO: 5 is C.

(6) Homozygous for the allele wherein the portion corresponding to positions 55-72 of SEQ ID NO: 6 is deleted.

(7) Homozygous for the allele wherein the base at the position corresponding to position 50 of SEQ ID NO: 7 is A.

[6] The kit according to [5], wherein the reagent comprises a primer and/or a probe for use in CAPS method, dCAPS method or TaqMan PCR method.

[7] A stevia plant with high rebaudioside M content ratio having at least one of the following genetic features (1) and (2), and at least one of the following genetic features (3) to (7).

(1) Homozygous for the allele wherein the base at the position corresponding to position 290 of SEQ ID NO: 1 is T.

(2) Homozygous for the allele wherein the base at the position corresponding to position 33 of SEQ ID NO: 2 is A.

(3) Homozygous for the allele wherein the base at the position corresponding to position 44 of SEQ ID NO: 3 is T.

(4) Homozygous for the allele wherein the base at the position corresponding to position 40 of SEQ ID NO: 4 is T.

(5) Homozygous for the allele wherein the base at the position corresponding to position 48 of SEQ ID NO: 5 is C.

(6) Homozygous for the allele wherein the portion corresponding to positions 55-72 of SEQ ID NO: 6 is deleted.

(7) Homozygous for the allele wherein the base at the position corresponding to position 50 of SEQ ID NO: 7 is A.

[8] The plant according to [7], wherein the plant is a non-genetically modified plant.

[9] The plant according to [7] or [8], wherein the plant includes a stevia plant subjected to a mutagenesis treatment and a progeny plant thereof.

[10] A seed, a tissue, a dried leaf, a tissue culture or a cell of the plant according to any one of [7] to [9].

[11] The tissue, tissue culture or cell according to [10], which is selected from an embryo, a meristem cell, a pollen, a leaf, a root, a root apex, a petal, a protoplast, a leaf section and a callus.

[12] A method of producing a stevia plant with high rebaudioside M content ratio, the method comprising a step of crossing the plant according to any one of [7] to [9] with a second stevia plant.

[13] The method according to [12], wherein the second plant is the plant according to any one of [7] to [9].

[14] A method of producing a stevia plant with high rebaudioside M content ratio, comprising a step of modifying the genome of a stevia plant such that the genome has at least one of the following genetic features (1) and (2) and at least one of the following genetic features (3) to (7).

(1) Homozygous for the allele wherein the base at the position corresponding to position 290 of SEQ ID NO: 1 is T.

(2) Homozygous for the allele wherein the base at the position corresponding to position 33 of SEQ ID NO: 2 is A.

(3) Homozygous for the allele wherein the base at the position corresponding to position 44 of SEQ ID NO: 3 is T.

(4) Homozygous for the allele wherein the base at the position corresponding to position 40 of SEQ ID NO: 4 is T.

(5) Homozygous for the allele wherein the base at the position corresponding to position 48 of SEQ ID NO: 5 is C.

(6) Homozygous for the allele wherein the portion corresponding to positions 55-72 of SEQ ID NO: 6 is deleted.

(7) Homozygous for the allele wherein the base at the position corresponding to position 50 of SEQ ID NO: 7 is A.

[15] The method according to [14], wherein the modification of the genome is performed by a mutagenesis treatment.

[16] An extract of the plant according to any one of [7] to [9], or of the seed, tissue, dried leaf, tissue culture or cell according to [10] or [11], wherein the extract comprises rebaudioside M at a high content ratio.

[17] A method of producing an extract comprising rebaudioside M at a high content ratio, comprising a step of obtaining an extract from the plant according to any one of [7] to [9], or from the seed, tissue, dried leaf, tissue culture or cell according to [10] or [11].

[18] A method of producing rebaudioside M, comprising a step of purifying rebaudioside M from the extract according to [16].

[19] A method of producing a food or beverage, a sweetener composition, a flavor or a medicament, comprising:

a step of providing an extract of the plant according to any one of [7] to [9], an extract of the seed, tissue, dried leaf, tissue culture or cell according to [10] or [11], or the extract according to [16]; and a step of adding the extract to a raw material for the food or beverage, sweetener composition, flavor or medicament.

Advantageous Effects of Invention

The present invention enables the obtainment of a stevia plant with higher RebM content ratio and the provision of an approach for producing such a plant, a leaf obtainable from such a plant, and a food, a drink, etc. containing RebM obtained from this leaf.

BRIEF DESCRIPTION OF DRAWINGS

FIG. 1 is a diagram showing the position of the base related to the genetic feature (1) in the nucleotide sequence of SEQ ID NO: 1. The boxed base is a base related to the genetic feature (1).

FIG. 2 is a diagram showing the position of the base related to the genetic feature (2) in the nucleotide sequence of SEQ ID NO: 2. The boxed base is a base related to the genetic feature (2).

FIG. 3 is a diagram showing the position of the base related to the genetic feature (3) in the nucleotide sequence of SEQ ID NO: 3. The boxed base is a base related to the genetic feature (3).

FIG. 4 is a diagram showing the position of the base related to the genetic feature (4) in the nucleotide sequence of SEQ ID NO: 4. The boxed base is a base related to the genetic feature (4).

FIG. 5 is a diagram showing the position of the base related to the genetic feature (5) in the nucleotide sequence of SEQ ID NO: 5. The boxed base is a base related to the genetic feature (5).

FIG. 6 is a diagram showing the position of the base related to the genetic feature (6) in the nucleotide sequence of SEQ ID NO: 6. The boxed base is a base related to the genetic feature (6).

FIG. 7 is a diagram showing the position of the base related to the genetic feature (7) in the nucleotide sequence of SEQ ID NO: 7. The boxed base is a base related to the genetic feature (7).

DESCRIPTION OF EMBODIMENTS

Hereinafter, the present invention will be described in detail. The embodiments are given below merely for illustrating the present invention and are not intended to limit the present invention by such embodiments. The present invention can be carried out in various modes without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2020-084129, filed on May 12, 2020, from which the present application claims priority.

1. Stevia Plant with High RebM Content Ratio

The present invention provides a stevia plant with high RebM content ratio having at least one of the following genetic features (1) and (2), and at least one of the following genetic features (3) to (7) (hereinafter, generically referred to as the "plant of the present invention" or "stevia plant of the present invention").

(1) Homozygous for the allele wherein the base at the position corresponding to position 290 of SEQ ID NO: 1 is T.

(2) Homozygous for the allele wherein the base at the position corresponding to position 33 of SEQ ID NO: 2 is A.

(3) Homozygous for the allele wherein the base at the position corresponding to position 44 of SEQ ID NO: 3 is T.

(4) Homozygous for the allele wherein the base at the position corresponding to position 40 of SEQ ID NO: 4 is T.

(5) Homozygous for the allele wherein the base at the position corresponding to position 48 of SEQ ID NO: 5 is C.

(6) Homozygous for the allele wherein the portion corresponding to positions 55-72 of SEQ ID NO: 6 is deleted.

(7) Homozygous for the allele wherein the base at the position corresponding to position 50 of SEQ ID NO: 7 is A.

The plant of the present invention is derived from a stevia plant of wild species and has acquired at least one of the genetic features (1) and (2) and at least one of the genetic features (3) to (7), which result in an increase of the RebM content ratio (hereinafter, the combination of at least one of the genetic features (1) and (2) and at least one of the genetic features (3) to (7) is generically referred to as the "genetic features of the present invention").

The phrase "position (or portion) corresponding to" means the following. In case a sequence identical to a reference sequence (e.g., SEQ ID NOs: 1 to 7, etc.) is present in the genome, it means a position or a portion in the sequence (e.g., 290, 33, 44, 40, 48, 55-72, 50, etc.) present in the genome, and in case a sequence identical to the reference sequence is not present in the genome, it means a position or portion in a sequence in the genome corresponding to the reference sequence, which corresponds to the position or portion in the reference sequence. Whether or not a sequence identical to or corresponding to the reference sequence exists in the genome can be determined by, for example, amplifying genomic DNA of the stevia plant of interest with a primer capable of amplifying the reference sequence by PCR, sequencing the amplified product, and performing alignment analysis between the obtained sequence and the reference sequence. Non-limiting examples of a sequence corresponding to a reference sequence include, for example, a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the reference sequence. The position or portion corresponding to the position or portion in the reference sequence in the sequence corresponding to the reference sequence in the genome can be determined by taking into account the nucleotide sequence before and after the position or portion in the reference sequence and the like. For example, a position or portion in the sequence corresponding to the reference sequence in the genome corresponding to a position or portion in the reference sequence can be determined by an alignment analysis of a reference sequence with a sequence corresponding to a reference sequence in the genome.

For instance, when taking "the position corresponding to position 290 of SEQ ID NO: 1" of the genetic feature (A) of the present invention as an example, in case the genome of a stevia plant has a portion consisting of a nucleotide sequence identical to SEQ ID NO: 1, "the position corresponding to position 290 of SEQ ID NO: 1" is position 290 from the 5' end of the portion consisting of a nucleotide sequence identical to SEQ ID NO: 1 in the genome. On the other hand, in case the genome of a stevia plant has a portion consisting of a nucleotide sequence which is not identical to, but which corresponds to SEQ ID NO: 1, the genome does not have a portion consisting of a nucleotide sequence identical to SEQ ID NO: 1. Therefore, "the position corresponding to position 290 of SEQ ID NO: 1" does not necessarily correspond to position 290 from the 5' end of the portion corresponding to SEQ ID NO: 1. However, it is possible to identify "the position corresponding to position 290 of SEQ ID NO: 1" in the genome of such a stevia plant by taking into account the nucleotide sequence before and after the position 290 of SEQ ID NO: 1, and the like. For instance, one can identify "the position corresponding to position 290 of SEQ ID NO: 1" in the genome of a stevia plant by an alignment analysis of the nucleotide sequence of a portion corresponding to SEQ ID NO: 1 in the genome of a stevia plant and the nucleotide sequence of SEQ ID NO: 1.

"The portion consisting of a nucleotide sequence corresponding to SEQ ID NO: 1" means, for instance, a portion consisting of a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the nucleotide sequence of SEQ ID NO: 1.

In some embodiments, "the portion consisting of a nucleotide sequence corresponding to SEQ ID NO: 1" includes a portion of the genome of a stevia plant which can be amplified by PCR using a forward primer (e.g., the one having the sequence of SEQ ID NO: 8) which hybridizes to a complementary sequence of a portion of positions 1 to 289 from the 5' end of SEQ ID NO: 1 (i.e., from the 5' end of SEQ ID NO: 1 to the base upstream by one base relative to the position 290 which relates to the genetic feature (1)) and a reverse primer (e.g., the one having the sequence of SEQ ID NO: 9) which hybridizes to a portion of positions 1 to 36 from the 3' end of SEQ ID NO: 1 (i.e., from the 3' end of SEQ ID NO: 1 to the base downstream by one base relative to the position 290 which relates to the genetic feature (1)).

In some embodiments, "the portion consisting of a nucleotide sequence corresponding to SEQ ID NO: 2" includes a portion of the genome of a stevia plant which can be amplified by PCR using a forward primer (e.g., the one having the sequence of SEQ ID NO: 10) which hybridizes to a complementary sequence of a portion of positions 1 to 32 from the 5' end of SEQ ID NO: 2 (i.e., from the 5' end of SEQ ID NO: 2 to the base upstream by one base relative to the position 33 which relates to the genetic feature (2)) and a reverse primer (e.g., the one having the sequence of SEQ ID NO: 11) which hybridizes to a portion of positions 1 to 37 from the 3' end of SEQ ID NO: 2 (i.e., from the 3' end of SEQ ID NO: 2 to the base downstream by one base relative to the position 33 which relates to the genetic feature (2)).

In some embodiments, "the portion consisting of a nucleotide sequence corresponding to SEQ ID NO: 3" includes a portion of the genome of a stevia plant which can be amplified by PCR using a forward primer (e.g., the one having the sequence of SEQ ID NO: 12) which hybridizes to a complementary sequence of a portion of positions 1 to 43 from the 5' end of SEQ ID NO: 3 (i.e., from the 5' end of SEQ ID NO: 3 to the base upstream by one base relative to the position 44 which relates to the genetic feature (3)) and a reverse primer (e.g., the one having the sequence of SEQ ID NO: 13) which hybridizes to a portion of positions 1 to 339 from the 3' end of SEQ ID NO: 3 (i.e., from the 3' end of SEQ ID NO: 3 to the base downstream by one base relative to the position 44 which relates to the genetic feature (3)).

In some embodiments, "the portion consisting of a nucleotide sequence corresponding to SEQ ID NO: 4" includes a portion of the genome of a stevia plant which can be amplified by PCR using a forward primer (e.g., the one having the sequence of SEQ ID NO: 14) which hybridizes to a complementary sequence of a portion of positions 1 to 39 from the 5' end of SEQ ID NO: 4 (i.e., from the 5' end of SEQ ID NO: 4 to the base upstream by one base relative to the position 40 which relates to the genetic feature (4)) and a reverse primer (e.g., the one having the sequence of SEQ ID NO: 15) which hybridizes to a portion of positions 1 to 257 from the 3' end of SEQ ID NO: 4 (i.e., from the 3' end of SEQ ID NO: 4 to the base downstream by one base relative to the position 40 which relates to the genetic feature (4)).

In some embodiments, "the portion consisting of a nucleotide sequence corresponding to SEQ ID NO: 5" includes a portion of the genome of a stevia plant which can be amplified by PCR using a forward primer (e.g., the one having the sequence of SEQ ID NO: 16) which hybridizes to a complementary sequence of a portion of positions 1 to 47 from the 5' end of SEQ ID NO: 5 (i.e., from the 5' end of SEQ ID NO: 5 to the base upstream by one base relative to the position 48 which relates to the genetic feature (5)) and a reverse primer (e.g., the one having the sequence of SEQ ID NO: 17) which hybridizes to a portion of positions 1 to 342 from the 3' end of SEQ ID NO: 5 (i.e., from the 3' end of SEQ ID NO: 5 to the base downstream by one base relative to the position 48 which relates to the genetic feature (5)).

In some embodiments, "the portion consisting of a nucleotide sequence corresponding to SEQ ID NO: 6" includes a portion of the genome of a stevia plant which can be amplified by PCR using a forward primer (e.g., the one having the sequence of SEQ ID NO: 18) which hybridizes to a complementary sequence of a portion of positions 1 to 54 from the 5' end of SEQ ID NO: 6 (i.e., from the 5' end of SEQ ID NO: 6 to the base corresponding to abase upstream by one base relative to the position 55 which is a position upstream of the portion related to the genetic feature (6)) and a reverse primer (e.g., the one having the sequence of SEQ ID NO: 19) which hybridizes to a portion of positions 1 to 86 from the 3' end of SEQ ID NO: 6 (i.e., from the 3' end of SEQ ID NO: 6 to the base corresponding to a base downstream by one base relative to the position 72 which is a position downstream of the portion related to the genetic feature (6)).

In some embodiments, "the portion consisting of a nucleotide sequence corresponding to SEQ ID NO: 7" includes a portion of the genome of a stevia plant which can be amplified by PCR using a forward primer (e.g., the one having the sequence of SEQ ID NO: 20) which hybridizes to a complementary sequence of a portion of positions 1 to 49 from the 5' end of SEQ ID NO: 7 (i.e., from the 5' end of SEQ ID NO: 7 to the base upstream by one base relative to the position 50 which relates to the genetic feature (7)) and a reverse primer (e.g., the one having the sequence of SEQ ID NO: 21) which hybridizes to a portion of positions 1 to 238 from the 3' end of SEQ ID NO: 7 (i.e., from the 3' end of SEQ ID NO: 7 to the base downstream by one base relative to the position 50 which relates to the genetic feature (7)).

In a specific embodiment, "the portion consisting of a nucleotide sequence corresponding to SEQ ID NO: 1" includes, for instance, a portion of the genome of a stevia plant which can be amplified by PCR using a forward primer comprising the nucleotide sequence of SEQ ID NO: 8 and a reverse primer comprising the nucleotide sequence of SEQ ID NO: 9.

In a specific embodiment, "the portion consisting of a nucleotide sequence corresponding to SEQ ID NO: 2" includes, for instance, a portion of the genome of a stevia plant which can be amplified by PCR using a forward primer comprising the nucleotide sequence of SEQ ID NO: 10 and a reverse primer comprising the nucleotide sequence of SEQ ID NO: 11.

In a specific embodiment, "the portion consisting of a nucleotide sequence corresponding to SEQ ID NO: 3" includes, for instance, a portion of the genome of a stevia plant which can be amplified by PCR using a forward primer comprising the nucleotide sequence of SEQ ID NO: 12 and a reverse primer comprising the nucleotide sequence of SEQ ID NO: 13.

In a specific embodiment, "the portion consisting of a nucleotide sequence corresponding to SEQ ID NO: 4" includes, for instance, a portion of the genome of a stevia plant which can be amplified by PCR using a forward primer comprising the nucleotide sequence of SEQ ID NO: 14 and a reverse primer comprising the nucleotide sequence of SEQ ID NO: 15.

In a specific embodiment, "the portion consisting of a nucleotide sequence corresponding to SEQ ID NO: 5" includes, for instance, a portion of the genome of a stevia plant which can be amplified by PCR using a forward primer comprising the nucleotide sequence of SEQ ID NO: 16 and a reverse primer comprising the nucleotide sequence of SEQ ID NO: 17.

In a specific embodiment, "the portion consisting of a nucleotide sequence corresponding to SEQ ID NO: 6" includes, for instance, a portion of the genome of a stevia plant which can be amplified by PCR using a forward primer comprising the nucleotide sequence of SEQ ID NO: 18 and a reverse primer comprising the nucleotide sequence of SEQ ID NO: 19.

In a specific embodiment, "the portion consisting of a nucleotide sequence corresponding to SEQ ID NO: 7" includes, for instance, a portion of the genome of a stevia plant which can be amplified by PCR using a forward primer comprising the nucleotide sequence of SEQ ID NO: 20 and a reverse primer comprising the nucleotide sequence of SEQ ID NO: 21.

In a specific embodiment, "the allele wherein the base at the position corresponding to position 290 of SEQ ID NO: 1 is T" (hereinafter, may be referred to as "allele related to the genetic feature (1)") comprises the nucleotide sequence of SEQ ID NO: 1, 22, 23 or 24.

In a specific embodiment, "the allele wherein the base at the position corresponding to position 33 of SEQ ID NO: 2 is A" (hereinafter, may be referred to as "allele related to the genetic feature (2)") comprises the nucleotide sequence of SEQ ID NO: 2, 25, 26 or 27.

In a specific embodiment, "the allele wherein the base at the position corresponding to position 44 of SEQ ID NO: 3 is T" (hereinafter, may be referred to as "allele related to the genetic feature (3)") comprises the nucleotide sequence of SEQ ID NO: 3, 28, 29 or 30.

In a specific embodiment, "the allele wherein the base at the position corresponding to position 40 of SEQ ID NO: 4 is T" (hereinafter, may be referred to as "allele related to the genetic feature (4)") comprises the nucleotide sequence of SEQ ID NO: 4, 31, 32 or 33.

In a specific embodiment, "the allele wherein the base at the position corresponding to position 48 of SEQ ID NO: 5 is C" (hereinafter, may be referred to as "allele related to the genetic feature (5)") comprises the nucleotide sequence of SEQ ID NO: 5, 34, 35 or 36.

In a specific embodiment, "the allele wherein the portion corresponding to positions 55-72 of SEQ ID NO: 6 is deleted" (hereinafter, may be referred to as "allele related to the genetic feature (6)") comprises the nucleotide sequence of SEQ ID NO: 99, 37, 38 or 39.

In a specific embodiment, "the allele wherein the base at the position corresponding to position 50 of SEQ ID NO: 7 is T" (hereinafter, may be referred to as "allele related to the genetic feature (7)") comprises the nucleotide sequence of SEQ ID NO: 7, 40, 41 or 42.

Here, (1) the position corresponding to position 290 of SEQ ID NO: 1, (2) the position corresponding to position 33 of SEQ ID NO: 2, (3) the position corresponding to position 44 of SEQ ID NO: 3, (4) the position corresponding to position 40 of SEQ ID NO: 4, (5) the position corresponding to position 48 of SEQ ID NO: 5, (6) the portion corresponding to positions 55-72 of SEQ ID NO: 6, (7) the position corresponding to position 50 of SEQ ID NO: 7 may be generically referred to as a "polymorphic site of the present invention" or a "site related to the genetic feature of the present invention".

The above genetic features can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNaPshot method, Mass ARRAY method, pyrosequencing method, SNP-IT method, melting curve analysis method, etc., but detection methods are not limited thereto.

In a specific embodiment, each genetic feature of the present invention is detectable by dCAPS method or the like using the following combination of a primer set and a restriction enzyme.

In case a candidate plant has the genetic feature (1), for example, a band of approximately 290 bp long (e.g., SEQ ID NO: 46) and a band of approximately 36 bp long (e.g., SEQ ID NO: 47) of almost the same density are obtained by: performing PCR amplification using a forward primer having the nucleotide sequence shown in SEQ ID NO: 43 and a reverse primer having the nucleotide sequence shown in SEQ ID NO: 44 on the genomic DNA of the candidate plant; and treating the obtained PCR product (approximately 326 bp long, e.g., SEQ ID NO: 45) with a restriction enzyme RsaI. On the other hand, in case the candidate plant does not have the genetic feature (1), a PCR product of approximately 326 bp long (e.g., SEQ ID NO: 48 or SEQ ID NOs: 45 and 48) is formed by performing PCR amplification in the same way as above, and when the PCR product is treated with the restriction enzyme, an uncleaved PCR product of approximately 326 bp long (e.g., SEQ ID NO: 48) is found.

In case a candidate plant has the genetic feature (2), for example, a band of approximately 30 bp long (e.g., SEQ ID NO: 52) and a band of approximately 166 bp long (e.g., SEQ ID NO: 53) are obtained by: performing PCR amplification using a forward primer having the nucleotide sequence shown in SEQ ID NO: 49 and a reverse primer having the nucleotide sequence shown in SEQ ID NO: 50 on the genomic DNA of the candidate plant; and treating the obtained PCR product (approximately 196 bp long, e.g., SEQ ID NO: 51) with a restriction enzyme MseI. On the other hand, in case the candidate plant does not have the genetic feature (2), a PCR product of approximately 196 bp long (e.g., SEQ ID NO: 54 or SEQ ID NOs: 51 and 54) is formed by performing PCR amplification in the same way as above, and when the PCR product is treated with the restriction enzyme, an uncleaved PCR product of approximately 196 bp long (e.g., SEQ ID NO: 54) is found.

In case a candidate plant has the genetic feature (3), for example, when performing PCR amplification using a forward primer having the nucleotide sequence shown in SEQ ID NO: 55 and a reverse primer having the nucleotide sequence shown in SEQ ID NO: 56 on the genomic DNA of the candidate plant, and treating the obtained PCR product (approximately 383 bp long, e.g., SEQ ID NO: 57) with a restriction enzyme XbaI, the PCR product is not cleaved, and only a band of approximately 383 bp long (e.g., SEQ ID NO: 57) is obtained. On the other hand, in case the candidate plant does not have the genetic feature (3) (the candidate plant has the allele wherein the base at the position corresponding to position 44 of SEQ ID NO: 3 is A), a PCR product of approximately 383 bp long (e.g., SEQ ID NO: 58 or SEQ ID NOs: 57 and 58) is formed by performing PCR amplification in the same way as above, and treating the obtained PCR product with a restriction enzyme XbaI, a restriction enzyme-treated product of approximately 344 bp long (e.g., SEQ ID NO: 59) is formed.

In case a candidate plant has the genetic feature (4), for example, when performing PCR amplification using a forward primer having the nucleotide sequence shown in SEQ ID NO: 60 and a reverse primer having the nucleotide sequence shown in SEQ ID NO: 61 on the genomic DNA of the candidate plant, and treating the obtained PCR product (approximately 297 bp long, e.g., SEQ ID NO: 62) with a restriction enzyme KpnI, the PCR product is not cleaved, and only a band of approximately 297 bp long (e.g., SEQ ID NO: 62) is obtained. On the other hand, in case the candidate plant does not have the genetic feature (4) (the candidate plant has the allele wherein the base at the position corresponding to position 40 of SEQ ID NO: 4 is C), a PCR product of approximately 297 bp long (e.g., SEQ ID NO: 63 or SEQ ID NOs: 62 and 63) is formed by performing PCR amplification in the same way as above, and treating the obtained PCR product with a restriction enzyme KpnI, a restriction enzyme-treated product of approximately 258 bp long (e.g., SEQ ID NO: 64) is formed.

In case a candidate plant has the genetic feature (5), for example, when performing PCR amplification using a forward primer having the nucleotide sequence shown in SEQ ID NO: 65 and a reverse primer having the nucleotide sequence shown in SEQ ID NO: 66 on the genomic DNA of the candidate plant, and treating the obtained PCR product (approximately 390 bp long, e.g., SEQ ID NO: 67) with a restriction enzyme AflII, the PCR product is not cleaved, and only a band of approximately 390 bp long (e.g., SEQ ID NO: 67) is obtained. On the other hand, in case the candidate plant does not have the genetic feature (5) (the candidate plant has the allele wherein the base at the position corresponding to position 48 of SEQ ID NO: 5 is G), a PCR product of approximately 390 bp long (e.g., SEQ ID NO: 68 or SEQ ID NOs: 67 and 68) is formed by performing PCR amplification in the same way as above, and treating the obtained PCR product with a restriction enzyme AflII, a restriction enzyme-treated product of approximately 347 bp long (e.g., SEQ ID NO: 69) is formed.

In case a candidate plant has the genetic feature (6), for example, only a PCR product of approximately 140 bp (e.g., SEQ ID NO: 72) is formed by performing PCR amplification using a forward primer having the nucleotide sequence shown in SEQ ID NO: 70 and a reverse primer having the nucleotide sequence shown in SEQ ID NO: 71 on the genomic DNA of the candidate plant. On the other hand, in case the candidate plant does not have the genetic feature (6), a PCR product of 158 bp (e.g., SEQ ID NO: 73) is formed by performing PCR amplification in the same way as above.

In case a candidate plant has the genetic feature (7), for example, when performing PCR amplification using a forward primer having the nucleotide sequence shown in SEQ ID NO: 74 and a reverse primer having the nucleotide sequence shown in SEQ ID NO: 75 on the genomic DNA of the candidate plant, and treating the obtained PCR product (approximately 288 bp long, e.g., SEQ ID NO: 76) with a restriction enzyme PvuI, the PCR product is not cleaved, and only a band of approximately 288 bp long (e.g., SEQ ID NO: 76) is obtained. On the other hand, in case the candidate plant does not have the genetic feature (7) (the candidate plant has the allele wherein the base at the position corresponding to position 50 of SEQ ID NO: 7 is G), a PCR product of approximately 288 bp long (e.g., SEQ ID NO: 77 or SEQ ID NOs: 76 and 77) is formed by performing PCR amplification in the same way as above, and treating the obtained PCR product with a restriction enzyme PvuI, a restriction enzyme-treated product of approximately 240 bp long (e.g., SEQ ID NO: 78) is formed.

The term "approximately" as to bp long described above means±5 bp. The restriction enzyme treatment can be performed according to conditions recommended by the distributor of each restriction enzyme used.

In some embodiments, the plant of the present invention has a combination of the genetic feature (1) or (2), and any one of the genetic features (3) to (6). In some embodiments, the plant of the present invention has a combination of the genetic feature (1) or (2), and the genetic feature (7). In some embodiments, the plant of the present invention has a combination of the genetic features (1) and (2), and any one of the genetic features (3) to (6). In some embodiments, the plant of the present invention has a combination of the genetic features (1) and (2), and the genetic feature (7). In some embodiments, the plant of the present invention has a combination of the genetic feature (1), and any one of the genetic features (3) to (7). In some embodiments, the plant of the present invention has a combination of the genetic feature (2), and any one of the genetic features (3) to (7). In some embodiments, the plant of the present invention has a combination of the genetic features (1) and (2), and any one of the genetic features (3) to (7). In a specific embodiment, the plant of the present invention has a combination of the genetic feature (1), and any one of the genetic features (3) to (6). In a specific embodiments, the plant of the present invention has a combination of the genetic feature (2), and any one of the genetic features (3) to (6). In a specific embodiments, the plant of the present invention has a combination of the genetic feature (1) and the genetic feature (4). In a specific embodiments, the plant of the present invention has a combination of the genetic feature (2) and the genetic feature (4). In a specific embodiments, the plant of the present invention has a combination of the genetic feature (1) and the genetic feature (7). In a specific embodiments, the plant of the present invention has a combination of the genetic feature (2) and the genetic feature (7). In a specific embodiment, the plant of the present invention has a combination of the genetic features (1) and (2), and the genetic feature (4). In a specific embodiment, the plant of the present invention has a combination of the genetic features (1) and (2), and the genetic feature (7). In a specific embodiment, the plant of the present invention has a combination of the genetic features (1) and (2), and the genetic features (4) and (7).

The plant of the present invention is derived from a stevia plant of wild species and has acquired the above genetic features which result in an increase of the RebM content ratio. The genetic features may be the ones generated by a genetic modification approach or the ones generated by a non-genetic modification approach. Therefore, the plant of the present invention may be the one obtained by a genetic modification approach or a progeny thereof (hereinafter, may be referred to as "genetically modified plant") or the one obtained by a non-genetic modification approach or a progeny thereof (hereinafter, may be referred to as "non-genetically modified plant").

Herein, examples of the "non-genetic modification approach" include a method of inducing a variation in the gene of a host cell (or a host plant) without transfection with a foreign gene. Examples of such a method include a method of allowing a mutagen to act on a plant cell. Examples of such a mutagen include ethylmethanesulfonic acid (EMS) and sodium azide. For example, EMS can be used at a concentration such as 0.1%, 0.2%, 0.3%, 0.4%, 0.5%, 0.6%, 0.7%, 0.8%, 0.9%, or 1.0% to treat a plant cell. The treatment time is about 1 hour to about 48 hours, about 2 hours to about 36 hours, about 3 hours to about 30 hours, about 4 hours to about 28 hours, about 5 hours to about 26 hours, or about 6 hours to about 24 hours. The procedures themselves of the treatment are known in the art and can be performed by dipping a water-absorbed seed obtained through a water absorption process in a treatment solution containing the mutagen at the concentration described above for the treatment time described above.

Another example of the non-genetic modification approach includes a method of irradiating a plant cell with radiation or light beam such as X-ray, y ray, or ultraviolet ray. In the case of irradiation with ultraviolet ray, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity may be 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, or 1 to 10 Gr. The irradiation distance may be 1 cm to 200 m, 5 cm to 100 m, 7 cm to 75 m, 9 cm to 50 m, 10 cm to 30 m, 10 cm to 20 m, or 10 cm to 10 m. The irradiation time may be 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or light beam, or the state of the subject to be irradiated (cell, callus, or plant) and can be appropriately adjusted by those skilled in the art.

Approaches such as cell fusion, anther culture (haploid induction), and remote crossing (haploid induction) are also known in the art.

In general, plant cells may involve a mutation during culture. Therefore, it is preferred to regenerate a plant individual, for more stably maintaining the trait.

The scope of the present invention does not exclude a plant obtained by the ex-post facto genetic recombination (e.g., genome editing) with a non-genetically modified stevia plant as a host (e.g., a plant further provided with another trait by genetic recombination with the plant of the present invention as a host).

The plant of the present invention is of high RebM content ratio type. The RebM content ratio means the ratio of the content of RebM to the content of the whole steviol glycoside (e.g., TSG) or specific steviol glycoside (e.g., RebD). The content may be, for example, the mass or concentration of the glycoside of interest contained in a stevia dried leaf of a unit mass. The dried leaf refers to a leaf having a water content decreased to 10% by weight or less, 7% by weight or less, 5% by weight or less, 4% by weight or less, 3% by weight or less, 2% by weight or less or 1% by weight or less by drying a fresh leaf. Preferably, the water content of the dried leaf of the plant of the present invention is 3 to 4% by weight.

The stevia plant with a high RebM content ratio means that the RebM content ratio is high as compared with a stevia plant that does not have the genetic features of the present invention. The high RebM content ratio means that, for example, the average or median RebM content ratio of a population of the plants of the present invention is higher than that of a population of stevia plants that do not have the genetic features of the present invention, and/or is higher than that of a population of stevia plants having at least one of the genetic features (3) to (7) (e.g., a population of stevia plants selected by a screening method comprising a step of detecting the presence and/or the absence of at least one of the genetic features (3) to (7) but not comprising a step of detecting the presence and/or the absence of at least one of the genetic features (1) and (2)).

The total steviol glycoside (TSG) is a generic name for measurable steviol glycosides and includes neither an unknown steviol glycoside nor a steviol glycoside present at a level less than the detection limit. Preferably, the TSG is any combination of two or more members selected from the group consisting of RebA, RebB, RebC, RebD, RebE, RebF, RebG, RebI, RebJ, RebK, RebM, RebN, RebO, RebQ, RebR, dulcoside A, rubusoside, steviolmonoside, steviolbioside and stevioside. In a specific embodiment, the TSG consists of the combination of RebA, RebB, RebC, RebD, RebE, RebF, RebG, RebM, RebN and stevioside.

In some embodiments, the average RebM content ratio of the population of the plants of the present invention is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more than that of a population of stevia plants that do not have the genetic features of the present invention.

In some embodiments, the average RebM content ratio of the population of the plants of the present invention is higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more or about 100% or more than that of a population of stevia plants having at least one of the genetic features (3) to (7).

In a specific embodiment, the average of the ratio of RebM content to RebD content in the population of the plants of the present invention is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more than that of a population of stevia plants that do not have the genetic features of the present invention.

In a specific embodiment, the average of the ratio of RebM content to RebD content in the population of the plants of the present invention is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more than that of a population of stevia plants having at least one of the genetic features (3) to (7).

In a specific embodiment, the average of the ratio of RebM content to the contents of TSG (in particular RebA, RebB, RebC, RebD, RebE, RebF, RebG, RebM, RebN and stevioside) in the population of the plants of the present invention is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more, about 160% or more, about 165% or more, about 170% or more, about 171% or more, about 175% or more or about 180% or more than that of a population of stevia plants that do not have the genetic features of the present invention.

In a specific embodiment, the average of the ratio of RebM content to the content of TSG (in particular RebA, RebB, RebC, RebD, RebE, RebF, RebG, RebM, RebN and stevioside) in the population of the plants of the present invention is higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more or about 80% or more than that of a population of stevia plants having at least one of the genetic features (3) to (7).

In a specific embodiment, the average of the ratio of RebM content to RebD content in the population of the plants of the present invention having the combination of the genetic feature (1) and the genetic feature (7) is higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more, about 100% or more, about 103% or more, about 105% or more, about 108% or more, about 110% or more than that of a population of stevia plants that do not have the combination of the genetic feature (1) and the genetic feature (7).

In a specific embodiment, the average of the ratio of RebM content to RebD content in the population of the plants of the present invention having the combination of the genetic feature (1) and the genetic feature (7) is higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more, about 80% or more, about 82% or more or about 84% or more than that of a population of stevia plants having the genetic feature (7).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (1) and the genetic feature (7) is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more, about 160% or more, about 165% or more, about 171% or more, about 175% or more or about 180% or more than that of a population of stevia plants that do not have the combination of the genetic feature (1) and the genetic feature (7).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (1) and the genetic feature (7) is higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more or about 80% or more than that of a population of stevia plants having the genetic feature (7).

In a specific embodiment, the average of the ratio of RebM content to RebD content in the population of the plants of the present invention having the combination of the genetic feature (2) and at least one of the genetic features (3) to (6) is higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 147% or more, about 150% or more, about 155% or more or about 160% or more than that of a population of stevia plants that do not have the combination of the genetic feature (2) and at least one of the genetic features (3) to (6).

In a specific embodiment, the average of the ratio of RebM content to RebD content in the population of the plants of the present invention having the combination of the genetic feature (2) and at least one of the genetic features (3) to (6) is higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more or about 100% or more than that of a population of stevia plants having at least one of the genetic features (3) to (6).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (2) and at least one of the genetic features (3) to (6) is higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 61% or more, about 62% or more, about 64% or more, about 66% or more, about 68% or more or about 70% or more than that of a population of stevia plants that do not have the combination of the genetic feature (2) and at least one of the genetic features (3) to (6).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (2) and at least one of the genetic features (3) to (6) is higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more, about 35% or more, about 36% or more, about 37% or more, about 38% or more, about 39% or more or about 40% or more than that of a population of stevia plants having at least one of the genetic features (3) to (6).

In a specific embodiment, the average of the ratio of RebM content to RebD content in the population of the plants of the present invention having the combination of the genetic feature (2) and the genetic feature (7) is higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more, about 35% or more, about 36% or more, about 37% or more, about 38% or more, about 39% or more, about 40% or more, about 41% or more, about 42% or more, about 43% or more, about 44% or more, about 45% or more, about 46% or more, about 47% or more, about 48% or more, about 49% or more or about 50% or more than that of a population of stevia plants that do not have the combination of the genetic feature (2) and the genetic feature (7).

In a specific embodiment, the average of the ratio of RebM content to RebD content in the population of the plants of the present invention having the combination of the genetic feature (2) and the genetic feature (7) is higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more or about 35% or more than that of a population of stevia plants having the genetic feature (7).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (2) and the genetic feature (7) is higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more or about 60% or more than that of a population of stevia plants that do not have the combination of the genetic feature (2) and the genetic feature (7).

In a specific embodiment, the average of the ratio of RebM content to the content of TSG (in particular RebA, RebB, RebC, RebD, RebE, RebF, RebG, RebM, RebN and stevioside) in the population of the plants of the present invention having the combination of the genetic feature (2) and the genetic feature (7) is higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more or about 35% or more than that of a population of stevia plants having the genetic feature (7).

The steviol glycosides such as RebD and RebM can be extracted in the state of a liquid extract by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3, 199-209 (2010) or WO2010/038911, or a method described in Examples mentioned later.

Individual steviol glycosides, for example, RebD and RebM, can be further purified from the liquid extract thus obtained by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC).

The contents of the steviol glycosides such as RebD and RebM can be measured by a method described in Ohta et al., supra or WO2010/038911, or a method described in Examples mentioned later. Specifically, for instance, a fresh leaf can be sampled from the stevia plant of the present invention, followed by measurement by LC-MS/MS and the like.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like. The leaf may be a dried leaf mentioned above.

The plant of the present invention may also include a tissue culture or a cultured plant cell. This is because the plant can be regenerated by culturing such a tissue culture or a cultured plant cell. Examples of a regenerable form of the plant of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing a stevia plant with high RebM content ratio, the method comprising a step of crossing the stevia plant of the present invention with a second stevia plant (hereinafter, may be referred to as the "production method of the present invention").

The stevia plant with high RebM content ratio produced by the method has the same phenotype and genetic features as those of the plant of the present invention. The level of RebM content ratio and the combination of the genetic features are as described above about the plant of the present invention.

In the production method of the present invention, "hybridizing" means that the plant of the present invention (first generation (S1)) is crossed with a second plant (S1) to obtain a progeny plant thereof (plant produced by the production method of the present invention (second generation (S2)). The hybridizing method is preferably backcross. The "backcross" is an approach of further crossing a progeny plant (S2) generated between the plant of the present invention and the second plant, with the plant of the present invention (i.e., a plant having the genetic feature(s) of the present invention) (S1) to produce a plant having the genetic feature(s) of the present invention. When the second plant (S1) for use in the production method of the present invention has the same phenotype and genetic features as those of the plant of the present invention, the crossing is substantially backcross.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic features as those of the plant of the present invention, the plant produced by the production method of the present invention can be further crossed with a third stevia plant to produce a stevia plant having a phenotype equivalent to that of the plant of the present invention.

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type stevia plant and are known in the art (Protocols for in vitro cultures and secondary metabolite analysis of aromatic and medicinal plants, Method in molecular biology, vol. 1391, pp. 113-123).

In a further alternative embodiment, the plant of the present invention may be produced by modifying the genome of a stevia plant so that the stevia plant is allowed to acquire the genetic features of the present invention. The acquirement of the genetic features of the present invention may be performed by a genetic modification approach or may be performed by a non-genetic modification approach. Examples of the non-genetic modification approach include mutagenesis treatment such as treatment with a mutagen and treatment by irradiation with radiation or light beam described in the section relating to the plant of the present invention. Specifically, for example, the genetic features of the present invention can be provided: to an individual having the allele wherein the base at the position corresponding to position 290 of SEQ ID NO: 1 is not T (e.g., the allele wherein the base at this position is C), by the substitution of the base at this position with T; to an individual having the allele wherein the base at the position corresponding to position 33 of SEQ ID NO: 2 is not A (e.g., the allele wherein the base at this position is T), by the substitution of the base at this position with A; to an individual having the allele wherein the base at the position corresponding to position 44 of SEQ ID NO: 3 is not T (e.g., the allele wherein the base at this position is A), by the substitution of the base at this position with T; to an individual having the allele wherein the base at the position corresponding to position 40 of SEQ ID NO: 4 is not T (e.g., the allele wherein the base at this position is C), by the substitution of the base at this position with T; to an individual having the allele wherein the base at the position corresponding to position 48 of SEQ ID NO: 5 is not C (e.g., the allele wherein the base at this position is G), by the substitution of the base at this position with C; to an individual having the allele wherein the portion corresponding to positions 55-72 of SEQ ID NO: 6 is not deleted, by the deletion of this portion; to an individual having the allele wherein the base at the position corresponding to position 50 of SEQ ID NO: 7 is not A (e.g., the allele wherein the base at this position is G), by the substitution of the base at this position with A.

3. Method of Screening for Plant of Present Invention

The plant of the present invention or the plant having the same phenotype and/or genetic feature as those of the plant of the present invention can be screened for by detecting the genetic feature(s) of the present invention from a tissue of this plant. In this context, "screening" means that the plant of the present invention is discriminated from the other plants to select the plant of the present invention.

Thus, in an alternative aspect, the present invention provides a method of screening for a stevia plant with high RebM content ratio, comprising a step of detecting the presence and/or the absence of at least one of the genetic features (1) and (2) and the presence and/or the absence of at least one of the genetic features (3) to (7) from the genome of a test plant (hereinafter, may be referred to as the "screening method of the present invention").

In some embodiments, the genetic features to be detected are the combination of the genetic feature (1) or (2) and any one of the genetic features (3) to (6). In some embodiments, the genetic features to be detected are the combination of the genetic feature (1) or (2) and the genetic feature (7). In some embodiments, the genetic features to be detected are the combination of the genetic features (1) and (2) and any one of the genetic features (3) to (6). In some embodiments, the genetic features to be detected are the combination of the genetic features (1) and (2) and the genetic feature (7). In some embodiments, the genetic features to be detected are the combination of the genetic feature (1) and any one of the genetic features (3) to (7). In some embodiments, the genetic features to be detected are the combination of the genetic feature (2) and any one of the genetic features (3) to (7). In some embodiments, the genetic features to be detected are the combination of the genetic features (1) and (2) and any one of the genetic features (3) to (7). In a specific embodiment, the genetic features to be detected are the combination of the genetic feature (1) and any one of the genetic features (3) to (6). In a specific embodiment, the genetic features to be detected are the combination of the genetic feature (2) and any one of the genetic features (3) to (6). In a specific embodiment, the genetic features to be detected are the combination of the genetic feature (1) and the genetic feature (4). In a specific embodiment, the genetic features to be detected are the combination of the genetic feature (2) and the genetic feature (4). In a specific embodiment, the genetic features to be detected are the combination of the genetic feature (1) and the genetic feature (7). In a specific embodiment, the genetic features to be detected are the combination of the genetic feature (2) and the genetic feature (7). In a specific embodiment, the genetic features to be detected are the combination of the genetic features (1) and (2) and the genetic feature (4). In a specific embodiment, the genetic features to be detected are the combination of the genetic features (1) and (2) and the genetic feature (7). In a specific embodiment, the genetic features to be detected are the combination of the genetic features (1) and (2) and the genetic features (4) and (7).

The screening method of the present invention may further comprise a step of selecting from among the test plants a plant in which the presence of at least one genetic feature of the above is detected.

The presence of the genetic features of the present invention can be determined, for example, by detecting the presence of only an allele selected from the group consisting of:

- (I) an allele wherein the base at the position corresponding to position 290 of SEQ ID NO: 1 is T (e.g., an allele comprising the nucleotide sequence of SEQ ID NO: 1, 22, 23 or 24);
- (II) an allele wherein the base at the position corresponding to position 33 of SEQ ID NO: 2 is A (e.g., an allele comprising the nucleotide sequence of SEQ ID NO: 2, 25, 26 or 27);
- (III) an allele wherein the base at the position corresponding to position 44 of SEQ ID NO: 3 is T (e.g., an allele comprising the nucleotide sequence of SEQ ID NO: 3, 28, 29 or 30);
- (IV) an allele wherein the base at the position corresponding to position 40 of SEQ ID NO: 4 is T (e.g., an allele comprising the nucleotide sequence of SEQ ID NO: 4, 31, 32 or 33);
- (V) an allele wherein the base at the position corresponding to position 48 of SEQ ID NO: 5 is C (e.g., an allele comprising the nucleotide sequence of SEQ ID NO: 5, 34, 35 or 36);
- (VI) an allele wherein the portion corresponding to positions 55-72 of SEQ ID NO: 6 is deleted (e.g., an allele comprising the nucleotide sequence of SEQ ID NO: 99, 37, 38 or 39), and
- (VII) an allele wherein the base at the position corresponding to position 50 of SEQ ID NO: 7 is A (e.g., an allele comprising the nucleotide sequence of SEQ ID NO: 7, 40, 41 or 42), and/or detecting the absence of an allele selected from the group consisting of:

- (i) an allele wherein the base at the position corresponding to position 290 of SEQ ID NO: 1 is C (e.g., an allele comprising the nucleotide sequence of SEQ ID NO: 79, 80, 81 or 82);
- (ii) an allele wherein the base at the position corresponding to position 33 of SEQ ID NO: 2 is T (e.g., an allele comprising the nucleotide sequence of SEQ ID NO: 83, 84, 85 or 86);
- (iii) an allele wherein the base at the position corresponding to position 44 of SEQ ID NO: 3 is A (e.g., an allele comprising the nucleotide sequence of SEQ ID NO: 87, 88, 89 or 90);
- (iv) an allele wherein the base at the position corresponding to position 40 of SEQ ID NO: 4 is C (e.g., an allele comprising the nucleotide sequence of SEQ ID NO: 91, 92, 93 or 94);
- (v) an allele wherein the base at the position corresponding to position 48 of SEQ ID NO: 5 is G (e.g., an allele comprising the nucleotide sequence of SEQ ID NO: 95, 96, 97 or 98);
- (vi) an allele wherein the portion corresponding to positions 55-72 of SEQ ID NO: 6 is not deleted (e.g., an allele comprising the nucleotide sequence of SEQ ID NO: 6, 100, 101 or 102), and (vii) an allele wherein the base at the position corresponding to position 50 of SEQ ID NO: 7 is G (e.g., an allele comprising the nucleotide sequence of SEQ ID NO: 103, 104, 105 or 106).

The absence of the genetic features of the present invention can be determined, for example, by detecting the absence of an allele selected from the group consisting of:

(I) an allele wherein the base at the position corresponding to position 290 of SEQ ID NO: 1 is T (e.g., an allele comprising the nucleotide sequence of SEQ ID NO: 1, 22, 23 or 24);

(II) an allele wherein the base at the position corresponding to position 33 of SEQ ID NO: 2 is A (e.g., an allele comprising the nucleotide sequence of SEQ ID NO: 2, 25, 26 or 27);

(III) an allele wherein the base at the position corresponding to position 44 of SEQ ID NO: 3 is T (e.g., an allele comprising the nucleotide sequence of SEQ ID NO: 3, 28, 29 or 30);

(IV) an allele wherein the base at the position corresponding to position 40 of SEQ ID NO: 4 is T (e.g., an allele comprising the nucleotide sequence of SEQ ID NO: 4, 31, 32 or 33);

(V) an allele wherein the base at the position corresponding to position 48 of SEQ ID NO: 5 is C (e.g., an allele comprising the nucleotide sequence of SEQ ID NO: 5, 34, 35 or 36);

(VI) an allele wherein the portion corresponding to positions 55-72 of SEQ ID NO: 6 is deleted (e.g., an allele comprising the nucleotide sequence of SEQ ID NO: 99, 37, 38 or 39), and (VII) an allele wherein the base at the position corresponding to position 50 of SEQ ID NO: 7 is A (e.g., an allele comprising the nucleotide sequence of SEQ ID NO: 7, 40, 41 or 42), and/or detecting the presence of an allele selected from the group consisting of:

(i) an allele wherein the base at the position corresponding to position 290 of SEQ ID NO: 1 is C (e.g., an allele comprising the nucleotide sequence of SEQ ID NO: 79, 80, 81 or 82);

(ii) an allele wherein the base at the position corresponding to position 33 of SEQ ID NO: 2 is T (e.g., an allele comprising the nucleotide sequence of SEQ ID NO: 83, 84, 85 or 86);

(iii) an allele wherein the base at the position corresponding to position 44 of SEQ ID NO: 3 is A (e.g., an allele comprising the nucleotide sequence of SEQ ID NO: 87, 88, 89 or 90);

(iv) an allele wherein the base at the position corresponding to position 40 of SEQ ID NO: 4 is C (e.g., an allele comprising the nucleotide sequence of SEQ ID NO: 91, 92, 93 or 94);

(v) an allele wherein the base at the position corresponding to position 48 of SEQ ID NO: 5 is G (e.g., an allele comprising the nucleotide sequence of SEQ ID NO: 95, 96, 97 or 98);

(vi) an allele wherein the portion corresponding to positions 55-72 of SEQ ID NO: 6 is not deleted (e.g., an allele comprising the nucleotide sequence of SEQ ID NO: 6, 100, 101 or 102), and (vii) an allele wherein the base at the position corresponding to position 50 of SEQ ID NO: 7 is G (e.g., an allele comprising the nucleotide sequence of SEQ ID NO: 103, 104, 105 or 106).

Specific examples of methods of detecting the genetic features of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNaPshot method, Mass ARRAY method, pyrosequencing method, SNP-IT method, melting curve analysis method, etc.

In the case of PCR method, it is preferable to generate a primer such that the 3' end portion has a sequence complementary to the site related to the genetic feature of the present invention. By using a primer designed in this way, the polymerase extension reaction proceeds because the primer hybridizes completely to the template if the template sample has the allele related to the genetic feature of the present invention, whereas if the template does not have the allele related to the genetic feature of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has the allele related to the genetic feature of the present invention, and if the amplification product is not present, it can be judged that the template does not have the allele related to the genetic feature of the present invention.

Alternatively, the genetic feature(s) of the present invention can be detected by designing the primer sequence so that the site related to the genetic feature of the present invention and the primer sequence do not overlap and a nucleotide fragment comprising the allele related to the genetic feature of the present invention can be PCR amplified, and by sequencing the nucleotide sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqManPCR method uses fluorescently labeled allele-specific oligos and Taq DNA polymerases (Livak, K. J. Genet. Anal. 14, 143 (1999); Morris T. et al., J. Clin. Microbiol. 34, 2933 (1996)).

The sequencing method is a method of analyzing the presence or absence of the genetic feature by amplifying a region containing the site related to the genetic feature by PCR and sequencing the DNA sequence using a Dye Terminator or the like (Sambrook, Fritsch and Maniatis, "Molecular Cloning: A Laboratory Manual" 2nd Edition (1989), Cold Spring Harbor Laboratory Press).

A DNA microarray is one in which one end of a nucleotide probe is immobilized in an array on a support, and includes a DNA chip, a Gene chip, a microchip, a bead array, and the like. By using a probe containing a sequence complementary to a sequence comprising the allele related to the genetic feature of the present invention, the presence or absence of the genetic feature of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele having or not having the genetic feature such as SNPs and one invader probe to template DNA and the cleavage of DNA by Cleavase enzyme with a special endonuclease activity which cleaves a DNA by recognizing its structure (Livak, K. J. Biomol. Eng. 14, 143-149 (1999); Morris T. et al., J. Clin. Microbiol. 34, 2933 (1996); Lyamichev, V. et al., Science, 260, 778-783 (1993), and the like).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the genetic feature (1) of the present invention can be detected, for example, by dCAPS method using the following primer set and a restriction enzyme.

Primer Set:

A primer set comprising a forward primer comprising a sequence (e.g., SEQ ID NO: 43) of any continuous sequence of 15 bases or more which is positioned at the positions 1 to 289 of SEQ ID NO: 1 and a reverse primer comprising a continuous sequence of 15 to 36-base long from the 3' end of the sequence selected from SEQ ID NOs: 44, 107 and 108.

Restriction Enzyme:

A restriction enzyme for the primer set based on SEQ ID NO: 44 includes RsaI, a restriction enzyme for the primer set based on SEQ ID NO: 107 includes SnaI, and a restriction enzyme for the primer set based on SEQ ID NO: 108 includes AluI.

In one embodiment, the genetic feature (2) of the present invention can be detected, for example, by dCAPS method using the following primer set and a restriction enzyme.

Primer Set:

A primer set comprising a forward primer comprising a continuous sequence of 15 to 32-base long from the 3' end of the sequence selected from SEQ ID NOs: 49, 109 and 110 and a reverse primer comprising a sequence (e.g., SEQ ID NO: 50) complementary to any continuous sequence of 15 bases or more which is positioned at the positions 34 to 196 of SEQ ID NO: 51.

Restriction Enzyme:

A restriction enzyme for the primer set based on SEQ ID NO: 49 includes MseI, a restriction enzyme for the primer set based on SEQ ID NO: 109 includes NlaIII, and a restriction enzyme for the primer set based on SEQ ID NO: 110 includes Tsp45I.

In one embodiment, the genetic feature (3) of the present invention can be detected, for example, by dCAPS method using the following primer set and a restriction enzyme.

Primer Set:

A primer set comprising a forward primer comprising a continuous sequence of 15 to 43-base long from the 3' end of SEQ ID NO: 55 and a reverse primer comprising a sequence (e.g., SEQ ID NO: 56) complementary to any continuous sequence of 15 bases or more which is positioned at the positions 45 to 383 of SEQ ID NO: 3.

Restriction Enzyme: XbaI.

In one embodiment, the genetic feature (4) of the present invention can be detected, for example, by dCAPS method using the following primer set and a restriction enzyme.

Primer Set:

A primer set comprising a forward primer comprising a continuous sequence of 15 to 39-base long from the 3' end of SEQ ID NO: 60 and a reverse primer comprising a sequence (e.g., SEQ ID NO: 61) complementary to any continuous sequence of 15 bases or more which is positioned at the positions 41 to 297 of SEQ ID NO: 4.

Restriction Enzyme: KpnI.

In one embodiment, the genetic feature (5) of the present invention can be detected, for example, by dCAPS method using the following primer set and a restriction enzyme.

Primer Set:

A primer set comprising a forward primer comprising a continuous sequence of 15 to 47-base long from the 3' end of SEQ ID NO: 65 and a reverse primer comprising a sequence (e.g., SEQ ID NO: 66) complementary to any continuous sequence of 15 bases or more which is positioned at the positions 49 to 390 of SEQ ID NO: 5.

Restriction Enzyme: AflII.

In one embodiment, the genetic feature (6) of the present invention can be detected, for example, by PCR method using the following primer set.

Primer Set:

A primer set comprising a forward primer comprising a sequence (e.g., SEQ ID NO: 70) of any continuous sequence of 15 bases or more which is positioned at the positions 1 to 54 of SEQ ID NO: 6 and a reverse primer comprising a sequence (e.g., SEQ ID NO: 71) of any continuous sequence of 15 bases or more which is positioned at the positions 73 to 158 of SEQ ID NO: 6.

In one embodiment, the genetic feature (7) of the present invention can be detected, for example, by dCAPS method using the following primer set and a restriction enzyme.

Primer Set:

A primer set comprising a forward primer comprising a continuous sequence of 15 to 49-base long from the 3' end of SEQ ID NO: 74 and a reverse primer comprising a sequence (e.g., SEQ ID NO: 75) complementary to any continuous sequence of 15 bases or more which is positioned at the positions 51 to 288 of SEQ ID NO: 7.

Restriction Enzyme: PvuI.

The sequences of the primers can be optimized within a range that satisfies the conditions described above. For the optimization of primer design, see, for example, Sambrook and Russell, "Molecular Cloning: A Laboratory Manual" 3rd Edition (2001), Cold Spring Harbor Laboratory Press. Each of the primers may be 15 to 50-base long, 18 to 48-base long, 20 to 45-base long, 30 to 40-base long, or the like. The restriction enzyme for each primer set also includes other enzymes that recognize the same sequence and cleave the same site as in the above enzyme, or an isoschizomer of the above enzyme. It is also possible to design a primer set other than those described above on the basis of the genetic feature(s) of the present invention and select a restriction enzyme appropriate therefor.

In a specific embodiment, the genetic features (1) to (5) and (7) of the present invention can be detected, e.g., by dCAPS method using the primer set having the following sequence and restriction enzyme.

TABLE 1

Examples of combination of primer set and restriction enzyme for detecting genetic feature (1)

| Forward primer | Reverse primer | Restriction enzyme |
|---|---|---|
| SEQ ID NO: 43 | SEQ ID NO: 44 | RsaI |
| SEQ ID NO: 43 | SEQ ID NO: 107 | SnaI |
| SEQ ID NO: 43 | SEQ ID NO: 108 | AluI |

TABLE 2

| Examples of combination of primer set and restriction enzyme for detecting genetic feature (2) | | |
|---|---|---|
| Forward primer | Reverse primer | Restriction enzyme |
| SEQ ID NO: 49 | SEQ ID NO: 50 | MseI |
| SEQ ID NO: 109 | SEQ ID NO: 50 | NlaIII |
| SEQ ID NO: 110 | SEQ ID NO: 50 | Tsp45I |

TABLE 3

| Examples of combination of primer set and restriction enzyme for detecting genetic feature (3) to (5) or (7) | | | |
|---|---|---|---|
| Genetic feature | Forward primer | Reverse primer | Restriction enzyme |
| (3) | SEQ ID NO: 55 | SEQ ID NO: 56 | XbaI |
| (4) | SEQ ID NO: 60 | SEQ ID NO: 61 | KpnI |
| (5) | SEQ ID NO: 65 | SEQ ID NO: 66 | AflII |
| (7) | SEQ ID NO: 74 | SEQ ID NO: 75 | PvuI |

The combinations of the primer set and the restriction enzyme described above are mere examples, and other combinations of primer sets and restriction enzymes capable of detecting the genetic feature(s) of the present invention can be found by those skilled in the art.

In a specific embodiment, the genetic feature (6) of the present invention can be detected, e.g., by PCR method using the primer set having the following sequence.

TABLE 4

| Primer set for detecting genetic feature (6) | |
|---|---|
| Forward primer | Reverse primer |
| SEQ ID NO: 70 | SEQ ID NO: 71 |

The screening methods of the present invention may further comprise a step of determining the content of steviol glycoside (e.g., the content of RebM and the content of RebD or TSG) of a tissue (e.g., a leave) of the test stevia plant tissue for which the genetic features of the present invention have been detected. The determination of the content of steviol glycoside is as described in the section relating to the plant of the present invention. In this embodiment, the screening method of the present invention may be applied to daughter plants obtained by selecting individuals with a higher RebM content ratio from among the test stevia plants in which the genetic features of the present invention is/are detected, and crossing the selected individuals with another stevia plants. Thus, the screening method of the present invention may comprise one or more of the following steps.

(i) Detecting the genetic features of the present invention from the genome of a test stevia plant;

(ii) determining the content of steviol glycoside of the test stevia plant tissue in which the genetic features of the present invention have been detected;

(iii) selecting an individual with a higher RebM content ratio from among the test stevia plants in which the genetic features of the present invention have been detected;

(iv) crossing the selected individual with a higher RebM content ratio with another stevia plant;

(v) detecting the genetic features of the present invention from the genome of daughter plants obtained by crossing, (vi) measuring the content of steviol glycoside of the tissue of the daughter plants in which the genetic features of the present invention have been detected, (vii) selecting individuals having a higher RebM content ratio from among the daughter plants in which the genetic features of the present invention are detected.

Individuals with a high RebM content ratio of choice may be, for example, up to 50%, up to 40%, up to 30%, up to 20%, up to 10%, up to 5%, up to 4%, up to 3%, up to 2%, or up to 1% of the test stevia plants in which the genetic features of the present invention have been detected, with respect to the high RebM content ratio. Other stevia plants to be crossed may or may not contain the genetic feature(s) of the present invention. In the above embodiment, steps (iv) to (vii) can be repeated a plurality of times. In this way, stevia plants with a higher RebM content ratio can be screened.

In the screening method of the present invention, the test stevia plant may be a natural plant or a non-transgenic plant. Non-transgenic plants are as described in the section relating to the plant of the present invention.

In the screening method of the present invention, the test stevia plant may include a stevia plant subjected to a mutagenesis treatment and a progeny plant thereof. The induction of a variation is as described in the section relating to the plant of the present invention, and includes treatment with a mutagen, treatment with radiation or irradiation with light, and the like.

The present invention also provides the primer sets described above and combinations thereof, for example, the primer sets described above in Tables 1 to 4; and combinations of the primer set(s) described above in Tables 1 to 2 that detect at least one of the genetic features (1) and (2), and the primer set(s) described above in Tables 3 to 4 that detect at least one of the genetic features (3) to (7). The present invention further provides a primer set capable of amplifying a region having a nucleotide sequence selected from the group consisting of SEQ ID NOs: 1 to 7, 79, 83, 87, 91, 95, 99 and 103 by PCR, for example, a primer set with a forward primer comprising a nucleotide sequence of SEQ ID NO: 8, and a reverse primer comprising a nucleotide sequence of SEQ ID NO: 9; a primer set with a forward primer comprising a nucleotide sequence of SEQ ID NO: 10, and a reverse primer comprising a nucleotide sequence of SEQ ID NO: 11; a primer set with a forward primer comprising a nucleotide sequence of SEQ ID NO: 12, and a reverse primer comprising a nucleotide sequence of SEQ ID NO: 13; a primer set with a forward primer comprising a nucleotide sequence of SEQ ID NO: 14, and a reverse primer comprising a nucleotide sequence of SEQ ID NO: 15; a primer set with a forward primer comprising a nucleotide sequence of SEQ ID NO: 16, and a reverse primer comprising a nucleotide sequence of SEQ ID NO: 17; a primer set with a forward primer comprising a nucleotide sequence of SEQ ID NO: 18, and a reverse primer comprising a nucleotide sequence of SEQ ID NO: 19; a primer set with a forward primer comprising a nucleotide sequence of SEQ ID NO: 20, and a reverse primer comprising a nucleotide sequence of SEQ ID NO: 21. Furthermore, the present invention provides a combination of a primer set capable of amplifying a region having a nucleotide sequence of SEQ ID NO: 1, 2, 79 or 83 by PCR, and a primer set capable of amplifying a region having a nucleotide sequence selected from the group consisting of SEQ ID NOs: 3 to 7, 87, 91, 95, 99 and 103 by PCR, for example, a combination of (A) a primer set selected from a primer set with a forward primer comprising a nucleotide sequence of SEQ ID NO: 8, and a reverse primer comprising a nucleotide sequence of SEQ ID NO: 9; and a primer set with a forward primer comprising a nucleotide sequence of SEQ ID NO: 10, and a reverse primer comprising a nucleotide sequence of SEQ ID NO: 11; and (B) a primer set selected from a primer set with a forward primer comprising a nucleotide sequence of SEQ ID NO: 12, and a reverse primer comprising a nucleotide sequence of SEQ ID NO: 13; a primer set with a forward primer comprising a nucleotide sequence of SEQ ID NO: 14, and a reverse primer comprising a nucleotide sequence of SEQ ID NO: 15; a primer set with a forward primer comprising a nucleotide sequence of SEQ ID NO: 16, and a reverse primer comprising a nucleotide sequence of SEQ ID NO: 17; a primer set with a forward primer comprising a nucleotide sequence of SEQ ID NO: 18, and a reverse primer comprising a nucleotide sequence of SEQ ID NO: 19; a primer set with a forward primer comprising a nucleotide sequence of SEQ ID NO: 20, and a reverse primer comprising a nucleotide sequence of SEQ ID NO: 21.

In addition, the present invention provides a probe capable of detecting the presence and/or absence of the genetic features of the present invention, which may be referred to as the "probe of the present invention" hereinafter. The probe of the present invention may have a structure suitable for various detection methods (e.g., realtime PCR method such as TaqMan PCR method and the like) for the presence and/or absence of the genetic feature(s) of the present invention. For example, the probe of the present invention may comprise a nucleotide sequence complementary to a portion of a genome comprising a site related to the genetic feature of the present invention. Non-limiting examples of such probes include those comprising a sequence complementary to a nucleotide sequence selected from SEQ ID NOs: 22 to 42, 80 to 82, 84 to 86, 88 to 90, 92 to 94, 96 to 98, 100 to 102 and 104 to 106. Of these sequences, SEQ ID NOs: 22 to 42 are specific for alleles related to the genetic feature of the present invention, and SEQ ID NOs: 80 to 82, 84 to 86, 88 to 90, 92 to 94, 96 to 98, 100 to 102 and 104 to 106 are specific for alleles which are not the alleles related to the genetic feature of the present invention.

Further, SEQ ID NOs: 22 to 24 are specific for allele related to the genetic feature (1) of the present invention, SEQ ID NOs: 25 to 27 are specific for allele related to the genetic feature (2) of the present invention, SEQ ID NOs: 28 to 30 are specific for allele related to the genetic feature (3) of the present invention, SEQ ID NOs: 31 to 33 are specific for allele related to the genetic feature (4) of the present invention, SEQ ID NOs: 34 to 36 are specific for allele related to the genetic feature (5) of the present invention, SEQ ID NOs: 37 to 39 are specific for allele related to the genetic feature (6) of the present invention, SEQ ID NOs: 40 to 42 are specific for allele related to the genetic feature (7) of the present invention. On the other hand, SEQ ID NOs: 80 to 82 are specific for an allele which is not the allele related to the genetic feature (1) of the present invention, SEQ ID NOs: 84 to 86 are specific for an allele which is not the allele related to the genetic feature (2) of the present invention, SEQ ID NOs: 88 to 90 are specific for an allele which is not the allele related to the genetic feature (3) of the present invention, SEQ ID NOs: 92 to 94 are specific for an allele which is not the allele related to the genetic feature (4) of the present invention, SEQ ID NOs: 96 to 98 are specific for an allele which is not the allele related to the genetic feature (5) of the present invention, SEQ ID NOs: 100 to 102 are specific for an allele which is not the allele related to the genetic feature (6) of the present invention, and SEQ ID NOs: 104 to 106 are specific for an allele which is not the allele related to the genetic feature (7) of the present invention.

The presence of the genetic feature(s) of the present invention may be detected by detection of an allele related to the genetic feature of the present invention and/or undetection of an allele which is not an allele related to the genetic feature of the present invention, and the absence of the genetic feature(s) of the invention by undetection of an allele related to the genetic feature of the present invention or by detection of an allele which is not an allele related to the genetic feature of the present invention. The probes of the present invention preferably have a label. Non-limiting examples of such labels include fluorescent labels, luminescent labels, radioactive labels, dyes, enzymes, quenchers, binding moieties with detectable labels, and the like. In a specific embodiment, the probe of the present invention has a polynucleotide comprising a nucleotide sequence complementary to a sequence selected from SEQ ID NOs: 22 to 42, 80 to 82, 84 to 86, 88 to 90, 92 to 94, 96 to 98, 100 to 102 and 104 to 106 and a label.

The present invention also provides a kit comprising the above-mentioned primer set and a restriction enzyme appropriate therefor. In a specific embodiment, the kit of the present invention comprises a primer set comprising a combination of a forward primer and a reverse primer stated in the above Tables 1-3 and a restriction enzyme appropriate therefor.

The present invention also provides a kit comprising a primer set capable of amplifying by PCR a region having a nucleotide sequence selected from the group consisting of SEQ ID NOs: 1 to 7, 79, 83, 87, 91, 95, 99 and 103, and the above-mentioned probe of the present invention appropriate therefor.

These primer sets, probes and kits can be used to detect the genetic feature(s) of the present invention, used in the screening methods of the present invention, and the like. These primer sets and kits may also comprise an instruction including an explanation on the detection of genetic feature (s) of the present invention and on the screening method of the present invention, e.g., a written instruction, information of a site comprising information regarding the method of use (e.g., URL and 2D code), and media, e.g., a flexible disk, a CD, a DVD, a Blu-ray disk, a memory card, a USB memory, etc., having recorded thereon information regarding the method of use, and the like.

In some embodiments, the present invention provides a screening kit for the stevia plant with high RebM content ratio, comprising a reagent for detecting the presence and/or the absence of at least one of the genetic features (1) and (2), and a reagent for detecting the presence and/or the absence of at least one of the genetic features (3) to (7). The reagent may comprise a primer and/or a probe for use in CAPS method, dCAPS method or TaqMan PCR method. In a specific embodiment, the reagent for detecting the presence and/or the absence of at least one of the genetic features (1) and (2) comprises a combination of a primer set and a restriction enzyme for detecting at least one of the above genetic features (1) and (2) by the dCAPS method, for instance a combination of a primer set and a restriction enzyme stated in Tables 1 and 2, or a combination of a primer set that amplifies the site(s) related to at least one of the genetic features (1) and (2) (e.g., a site comprising a sequence selected from SEQ ID NOs: 1, 2 and 22 to 27), and a probe having a nucleotide sequence complementary to a site related to at least one of the genetic features (1) and (2) (e.g., a site comprising a sequence selected from SEQ ID NOs: 22 to 27), which can be used in the TaqMan PCR method or the like. In a specific embodiment, the reagent for detecting the presence and/or the absence of at least one of the genetic features (3) to (7) comprises a combination of a primer set and a restriction enzyme for detecting at least one of the above genetic features (3) to (5) and (7) by the dCAPS method, for instance a combination of a primer set and a restriction enzyme stated in Table 3, or a primer set for detecting the genetic feature (6) by PCR method mentioned above, or a combination of a primer set that amplifies the site(s) related to at least one of the genetic features (3) to (7) (e.g., a site comprising a sequence selected from SEQ ID NOs: 3 to 5, 99, 7 and 28 to 42), and a probe having a nucleotide sequence complementary to a site related to at least one of the genetic features (3) to (7) (e.g., a site comprising a sequence selected from SEQ ID NOs: 28 to 42), which can be used in the TaqMan PCR method or the like.

4. Method of Producing Extract Derived from Plant and Product Comprising the Extract In a further aspect, the present invention provides a method of producing an extract with high RebM content ratio, comprising a step of obtaining an extract from the plant of the present invention, a stevia plant selected by the screening method of the present invention or a stevia plant produced by the production method of the present invention, or a seed, a leaf (e.g., dried leaf or fresh leaf), a tissue, a tissue culture or a cell of the plant (hereinafter, may be referred to as the "extract production method of the present invention").

Further provided is an extract with high RebM content ratio from the plant of the present invention, a stevia plant selected by the screening method of the present invention or a stevia plant produced by the production method of the present invention, or a seed, a leaf (e.g., dried leaf or fresh leaf), a tissue, a tissue culture or a cell of the plant (hereinafter, may be referred to as the "extract of the present invention"). The extract of the present invention is preferably produced by the extract production method of the present invention. Furthermore provided is a method of producing RebM, comprising a step of purifying RebM from the extract of the present invention (hereinafter, may be referred to as the "RebM production method of the present invention"). The RebM production method of the present invention may further comprise a step of obtaining an extract with high RebM content ratio from the plant of the present invention, a stevia plant selected by the screening method of the present invention or a stevia plant produced by the production method of the present invention.

The extract with high RebM content ratio can be obtained by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al., supra or WO2010/038911, or a method described in Examples mentioned later. RebM can be purified from the extract with high RebM content ratio by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC).

The extract obtained by the extract production method of the present invention (hereinafter, referred to as the "extract of the present invention") comprises RebM at higher content ratio as compared with an extract obtained from a stevia plant not having the genetic feature of the present invention by the same process.

In some embodiments, the extract of the present invention has a RebM content ratio higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more as compared with an extract obtained from a stevia plant not having the genetic feature of the present invention.

In some embodiments, the extract of the present invention has a RebM content ratio higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more or about 100% or more as compared with an extract obtained from a stevia plant having at least one of the genetic features (3) to (7).

In a specific embodiment, the extract of the present invention has a ratio of RebM content to RebD content higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more as compared with an extract obtained from a stevia plant that do not have the genetic features of the present invention.

In a specific embodiment, the extract of the present invention has a ratio of RebM content to RebD content higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more or about 160% or more as compared with an extract obtained from a stevia plant having at least one of the genetic features (3) to (7).

In a specific embodiment, the extract of the present invention has a ratio of RebM content to the contents of TSG (in particular RebA, RebB, RebC, RebD, RebE, RebF, RebG, RebM, RebN and stevioside) higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more, about 160% or more, about 165% or more, about 170% or more, about 171% or more, about 175% or more or about 180% or more as compared with an extract obtained from a stevia plant that do not have the genetic features of the present invention.

In a specific embodiment, the extract of the present invention has a ratio of RebM content to the content of TSG (in particular RebA, RebB, RebC, RebD, RebE, RebF, RebG, RebM, RebN and stevioside) higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more or about 80% or more as compared with an extract obtained from a stevia plant having at least one of the genetic features (3) to (7).

In a specific embodiment, the extract obtained from the plant of the present invention having the combination of the genetic feature (1) and the genetic feature (7) has a ratio of RebM content to RebD content higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more, about 100% or more, about 103% or more, about 105% or more, about 108% or more, about 110% or more as compared with an extract obtained from a stevia plant that do not have the combination of the genetic feature (1) and the genetic feature (7).

In a specific embodiment, the extract obtained from the plant of the present invention having the combination of the genetic feature (1) and the genetic feature (7) has a ratio of RebM content to RebD content higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more, about 80% or more, about 82% or more or about 84% or more as compared with an extract obtained from a stevia plant having the genetic feature (7).

In a specific embodiment, the extract obtained from the plant of the present invention having the combination of the genetic feature (1) and the genetic feature (7) has a ratio of RebM content to the content of TSG (in particular RebA, RebB, RebC, RebD, RebE, RebF, RebG, RebM, RebN and stevioside) higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 150% or more, about 155% or more, about 160% or more, about 165% or more, about 171% or more, about 175% or more or about 180% or more as compared with an extract obtained from a stevia plant that do not have the combination of the genetic feature (1) and the genetic feature (7).

In a specific embodiment, the extract obtained from the plant of the present invention having the combination of the genetic feature (1) and the genetic feature (7) has a ratio of RebM content to the content of TSG (in particular RebA, RebB, RebC, RebD, RebE, RebF, RebG, RebM, RebN and stevioside) higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 66% or more, about 68% or more, about 70% or more, about 72% or more, about 74% or more, about 76% or more, about 78% or more or about 80% or more as compared with an extract obtained from a stevia plant having the genetic feature (7).

In a specific embodiment, the extract obtained from the plant of the present invention having the combination of the genetic feature (2) and at least one of the genetic features (3) to (6) has a ratio of RebM content to RebD content higher by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 100% or more, about 105% or more, about 110% or more, about 115% or more, about 120% or more, about 125% or more, about 130% or more, about 135% or more, about 140% or more, about 145% or more, about 147% or more, about 150% or more, about 155% or more or about 160% or more as compared with an extract obtained from a stevia plant that do not have the combination of the genetic feature (2) and at least one of the genetic features (3) to (6).

In a specific embodiment, the extract obtained from the plant of the present invention having the combination of the genetic feature (2) and at least one of the genetic features (3) to (6) has a ratio of RebM content to RebD content higher by about 10% or more, about 13% or more, about 15% or more, about 18% or more, about 20% or more, about 23% or more, about 25% or more, about 28% or more, about 30% or more, about 33% or more, about 35% or more, about 38% or more, about 40% or more, about 43% or more, about 45% or more, about 48% or more, about 50% or more, about 53% or more, about 55% or more, about 58% or more, about 60% or more, about 63% or more, about 65% or more, about 68% or more, about 70% or more, about 73% or more, about 75% or more, about 78% or more, about 80% or more, about 83% or more, about 85% or more, about 88% or more, about 90% or more, about 93% or more, about 95% or more, about 98% or more or about 100% or more as compared with an extract obtained from a stevia plant having at least one of the genetic features (3) to (6).

In a specific embodiment, the extract obtained from the plant of the present invention having the combination of the genetic feature (2) and at least one of the genetic features (3) to (6) has a ratio of RebM content to the content of TSG (in particular RebA, RebB, RebC, RebD, RebE, RebF, RebG, RebM, RebN and stevioside) higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 61% or more, about 62% or more, about 64% or more, about 66% or more, about 68% or more or about 70% or more as compared with an extract obtained from a stevia plant that do not have the combination of the genetic feature (2) and at least one of the genetic features (3) to (6).

In a specific embodiment, the extract obtained from the plant of the present invention having the combination of the genetic feature (2) and at least one of the genetic features (3) to (6) has a ratio of RebM content to the content of TSG (in particular RebA, RebB, RebC, RebD, RebE, RebF, RebG, RebM, RebN and stevioside) higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more, about 35% or more, about 36% or more, about 37% or more, about 38% or more, about 39% or more or about 40% or more as compared with an extract obtained from a stevia plant having at least one of the genetic features (3) to (6).

In a specific embodiment, the extract obtained from the plant of the present invention having the combination of the genetic feature (2) and the genetic feature (7) has a ratio of RebM content to RebD content higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more, about 35% or more, about 36% or more, about 37% or more, about 38% or more, about 39% or more, about 40% or more, about 41% or more, about 42% or more, about 43% or more, about 44% or more, about 45% or more, about 46% or more, about 47% or more, about 48% or more, about 49% or more or about 50% or more as compared with an extract obtained from a stevia plant that do not have the combination of the genetic feature (2) and the genetic feature (7).

In a specific embodiment, the plant of the present invention having the combination of the genetic feature (2) and the genetic feature (7) has a ratio of RebM content to RebD content higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more or about 35% or more as compared with an extract obtained from a stevia plant having the genetic feature (7).

In a specific embodiment, the extract obtained from the plant of the present invention having the combination of the genetic feature (2) and the genetic feature (7) has a ratio of RebM content to the content of TSG (in particular RebA, RebB, RebC, RebD, RebE, RebF, RebG, RebM, RebN and stevioside) higher by about 10% or more, about 12% or more, about 14% or more, about 16% or more, about 18% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more or about 60% or more as compared with an extract obtained from a stevia plant that do not have the combination of the genetic feature (2) and the genetic feature (7).

In a specific embodiment, the extract obtained from the plant of the present invention having the combination of the genetic feature (2) and the genetic feature (7) has a ratio of RebM content to the content of TSG (in particular RebA, RebB, RebC, RebD, RebE, RebF, RebG, RebM, RebN and stevioside) higher by about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 31% or more, about 32% or more, about 33% or more, about 34% or more or about 35% or more as compared with an extract obtained from a stevia plant having the genetic feature (7).

The extract of the present invention thus obtained and/or RebM obtained by the RebM production method of the present invention can be mixed with other component(s) to produce a food or beverage, sweetener composition, flavor or medicament comprising RebM at high content ratio. Accordingly, in an alternative aspect, the present invention provides a method of producing a food or beverage, a sweetener composition, a flavor or a medicament, comprising a step of mixing the extract of the present invention, and/or RebM obtained by the RebM production method of the present invention with other component(s). The present invention further provides a food or beverage, sweetener composition, flavor or medicament with increased content of RebM, obtained by the production method. In this context, the food or beverage comprises a beverage and a food. Thus, in a certain embodiment, the present invention provides a beverage, food, sweetener composition, flavor or medicament and also provides a method of producing the beverage, food, sweetener composition, flavor or medicament.

5. Nucleotide Sequence Relating to Plant of Present Invention

In another aspect, the present invention provides nucleotide sequences relating to the stevia plant of the present invention.

A specific embodiment of nucleotide sequences relating to a stevia plant having the genetic feature (1) of the present invention comprises or consists of a nucleotide sequence selected from SEQ ID NOs: 1 and 22 to 24. A specific embodiment of nucleotide sequences relating to a stevia plant having the genetic feature (2) of the present invention comprises or consists of a nucleotide sequence selected from SEQ ID NOs: 2 and 25 to 27. A specific embodiment of nucleotide sequences relating to a stevia plant having the genetic feature (3) of the present invention comprises or consists of a nucleotide sequence selected from SEQ ID NOs: 3 and 28 to 30. A specific embodiment of nucleotide sequences relating to a stevia plant having the genetic feature (4) of the present invention comprises or consists of a nucleotide sequence selected from SEQ ID NOs: 4 and 31 to 33. A specific embodiment of nucleotide sequences relating to a stevia plant having the genetic feature (5) of the present invention comprises or consists of a nucleotide sequence selected from SEQ ID NOs: 5 and 34 to 36. A specific embodiment of nucleotide sequences relating to a stevia plant having the genetic feature (6) of the present invention comprises or consists of a nucleotide sequence selected from SEQ ID NOs: 99 and 37 to 39. A specific embodiment of nucleotide sequences relating to a stevia plant having the genetic feature (7) of the present invention comprises or consists of a nucleotide sequence selected from SEQ ID NOs: 7 and 40 to 42. A specific embodiment of nucleotide sequences relating to a stevia plant having at least one of the genetic features (1) and (2) and at least one of the genetic features (3) to (7) of the present invention comprises a nucleotide sequence selected from SEQ ID NOs: 1, 2 and 22 to 27 and a nucleotide sequence selected from SEQ ID NOs: 3 to 5, 99, 7 and 28 to 42.

EXAMPLES

Hereinafter, the present invention will be described with reference to Examples, etc. However, the present invention is not limited by these specific embodiments.

(1) Generation of Population with High Steviol Glycoside Content

A wild type stevia species (commercially available variety) was treated with ethyl methanesulfonate (EMS), and the resultant was seeded and cultivated in a greenhouse within the Suntory World Research Center. An appropriate amount of fresh leaves was sampled from each grown individual, and the concentration of steviol glycoside was quantitatively determined by LC-MS/MS (Shimadzu LCMS8050). Specifically, 0.25 g of the fresh leaves was dried by freeze drying, and 0.05 g of homogenized dry matter thereof was added into a 100-fold amount (5 mL) of pure water. Extraction by ultrasonic treatment for 20 minutes, and centrifugation and filtration were performed, followed by 60-fold dilution with 32% acetonitrile to obtain a liquid sample. The concentration of RebA, RebB, RebC, RebD, RebF, RebM, RebN, RebO and stevioside was quantitatively determined by LC/MS-MS analysis on this 1 mL of liquid sample in a LCMS8050 MRM mode, and individuals having the total concentration of about 5 to 20% were selected and crossed to obtain seeds. Such selection was repeated over four generations to obtain Populations A and B.

(2) Gene Analysis of Individuals with High RebM Content Ratio

An appropriate amount of fresh leaves was sampled from each individual of Populations A and B, and the concentrations of RebA, RebB, RebC, RebD, RebE, RebF, RebG, RebM, RebN and stevioside (TSG) were quantitatively determined by LC/MS-MS (Shimadzu LCMS8050) in the same way as in the preceding section (1). Also, genomic DNA was extracted from the fresh leaves of some individuals in both the populations, and genetically analyzed using a sequencer (HiSeq 2500, Illumina, Inc.). As a result, the average RebM content ratios (RebM/RebD and RebM/TSG) of the individual group having the genetic features of the present invention were found to tend to be higher than the average TSG contents of individual that did not have the genetic features of the present invention, all the individuals of the population A or B, and the individuals having the genetic features (3) to (7). Accordingly, in order to efficiently detect the genetic features, dCAPS primers for detecting the genetic features (1), (2), (4) and (7) were generated, and the remaining individuals were evaluated for the presence or absence of these genetic features by the dCAPS method. The study by the dCAPS method was omitted for the genetic features (3), (5) and (6), because these genetic features are known to exhibit similar behavior to that of the genetic feature (4) according to WO2019/074089.

The following dCAPS primers and restriction enzymes were used.

TABLE 5

Sequence of dCAPS primers and restriction enzyme

| Genetic feature | Forward primer | Reverse primer | Restriction enzyme |
|---|---|---|---|
| (1) | GGCAGCCATTGATGATGTTGTTGAA (SEQ ID NO: 43) | CCAATTCTCATAGAAAATATGATAGAATAAATGCGT (SEQ ID NO: 44) | RsaI |
| (2) | TGATTTTGAAAGGATCTGACTGTATGTTTTTA (SEQ ID NO: 49) | TGTTGACCATCAAGCCACAT (SEQ ID NO: 50) | MseI |
| (4) | TAATCATCCAAACCCTAATCTCGCCAAACAACCGGGTAC (SEQ ID NO: 60) | GAGGAAGACATTGGCAACTC (SEQ ID NO: 61) | KpnI |

TABLE 5-continued

Sequence of dCAPS primers and restriction enzyme

| Genetic feature | Forward primer | Reverse primer | Restriction enzyme |
|---|---|---|---|
| (7) | ATACAAAAACACAACCCATATGGTCAAATCAAC CCATTCATGAGCGATC (SEQ ID NO: 74) | CCCTTGTAAATCCCATATG TAG (SEQ ID NO: 75) | PvuI |

The detection of each genetic feature by the dCAPS method was performed as follows. First, genomic DNA was extracted from the fresh leaves of each individual of Populations A and B, and PCR was performed using the above dCAPS primers for each genetic feature. The above restriction enzyme for each genetic feature was added to the PCR product, and enzymatic reaction was performed at 37° C. The restriction enzyme-treated products were electrophoresed using a microchip type electrophoresis apparatus LabChip GX Touch HT (PerkinElmer, Inc.). The presence or absence of the genetic feature was determined on the basis of the obtained band pattern. Specifically, since all the genetic features (1), (2), (4) and (7) are homozygous, an individual for which only a band of a degradation product was found as to the genetic features (1) and (2) was determined as having the genetic features, while an individual for which only a band of a non-degradation product was found as to the genetic features (4) and (7) was determined as having the genetic features.

From the results shown in Tables 6 to 8, the tendency found by sequencing was confirmed. In the tables, (1), (2), (4) and (7) mean the genetic features (1), (2), (4) and (7), respectively; "Other than X" represents an individual that does not have the genetic feature X (e.g., "Other than (1)+(7)" represents an individual group other than individuals having the combination of the genetic feature (1) and the genetic feature (7)); and "(4)/(7)" represents an individual having at least one of the genetic feature (4) and the genetic feature (7). The increase rate represents the increase rate in RebM content ratio of an individual group having the genetic features of the present invention (an individual group having the genetic feature (1) and the genetic feature (7), an individual group having the genetic feature (2) and the genetic feature (4), or an individual group having the genetic feature (2) and the genetic feature (7)) with respect to the RebM content ratios of the other individual groups. Although the genetic features (4) and (7) are known as markers for the selections of a high RebM content stevia plant (Patent Literature 2), it is evident that their combinations with the genetic feature (1) or (2) of the present invention can select an individual with a higher RebM content ratio.

TABLE 6

RebM content ratio in Population A

| | All individuals | (7) | (1) + (7) | Other than (1) + (7) |
|---|---|---|---|---|
| RebM/RebD (%) | 25.0 | 27.9 | 49.1 | 24.0 |
| Increase rate (%) | 96.4 | 76.0 | | 104.6 |
| RebM/TSG (%) | 1.6 | 2.4 | 4.1 | 1.5 |
| Increase rate (%) | 152.8 | 70.2 | | 171.1 |

TABLE 7

RebM content ratio in Population B (1)

| | All individuals | (4) | (2) + (4) | Other than (2) + (4) | Other than (2) + (4)/(7) |
|---|---|---|---|---|---|
| RebM/RebD (%) | 21.0 | 22.4 | 43.3 | 17.5 | 17.3 |
| Increase rate (%) | 106.2 | 93.3 | | 147.4 | 150.3 |
| RebM/TSG (%) | 3.2 | 3.3 | 4.5 | 2.8 | 2.8 |
| Increase rate (%) | 40.1 | 36.7 | | 61.0 | 63.9 |

TABLE 8

RebM content ratio in Population B (2)

| | All individuals | (7) | (2) + (7) | Other than (2) + (7) | Other than (2) + (4)/(7) |
|---|---|---|---|---|---|
| RebM/RebD (%) | 21.0 | 22.5 | 29.5 | 20.0 | 17.3 |
| Increase rate (%) | 40.5 | 31.1 | | 47.5 | 70.5 |
| RebM/TSG (%) | 3.2 | 3.7 | 4.7 | 3.1 | 2.8 |
| Increase rate (%) | 45.4 | 29.0 | | 53.9 | 70.0 |

INDUSTRIAL APPLICABILITY

The present invention enables the more efficient provision of RebM and can therefore provide a food or beverage, a sweetener composition, a flavor or a medicament, etc. having good quality of taste by comprising sufficient amount of RebM.

The invention claimed is:

1. A method of screening for a stevia plant with high rebaudioside M content ratio, comprising detecting from the genome of a test stevia plant the presence and/or the absence of at least one of the following genetic features (1) and (2), and the presence and/or the absence of at least one of the following genetic features (3) to (7):

(1) homozygous for the allele wherein the base at the position corresponding to position 290 of SEQ ID NO: 1 is T;
(2) homozygous for the allele wherein the base at the position corresponding to position 33 of SEQ ID NO: 2 is A;
(3) homozygous for the allele wherein the base at the position corresponding to position 44 of SEQ ID NO: 3 is T;
(4) homozygous for the allele wherein the base at the position corresponding to position 40 of SEQ ID NO: 4 is T;
(5) homozygous for the allele wherein the base at the position corresponding to position 48 of SEQ ID NO: 5 is C;
(6) homozygous for the allele wherein the portion corresponding to positions 55-72 of SEQ ID NO: 6 is deleted;
(7) homozygous for the allele wherein the base at the position corresponding to position 50 of SEQ ID NO: 7 is A.

2. The method according to claim 1, further comprising measuring the content of rebaudioside M in a test stevia plant tissue in which the presence and/or the absence of the genetic features has/have been detected.

3. The method according to claim 1, wherein the rebaudioside M content ratio of the stevia plant with a high rebaudioside M content ratio is higher by 10% or more than that of a stevia plant selected by a screening method comprising detecting the presence and/or the absence of at least one of the genetic features (3) to (7) but not comprising detecting the presence and/or the absence of at least one of the genetic features (1) and (2).

4. The method according to claim 1, wherein the detecting the presence and/or the absence of the genetic features is performed by use of CAPS method, dCAPS method or TaqMan PCR method.

5. A stevia plant with high rebaudioside M content ratio having at least one of the following genetic features (1) and (2), and at least one of the following genetic features (3) to (7):

(1) homozygous for the allele wherein the base at the position corresponding to position 290 of SEQ ID NO: 1 is T;
(2) homozygous for the allele wherein the base at the position corresponding to position 33 of SEQ ID NO: 2 is A;
(3) homozygous for the allele wherein the base at the position corresponding to position 44 of SEQ ID NO: 3 is T;
(4) homozygous for the allele wherein the base at the position corresponding to position 40 of SEQ ID NO: 4 is T;
(5) homozygous for the allele wherein the base at the position corresponding to position 48 of SEQ ID NO: 5 is C;
(6) homozygous for the allele wherein the portion corresponding to positions 55-72 of SEQ ID NO: 6 is deleted;
(7) homozygous for the allele wherein the base at the position corresponding to position 50 of SEQ ID NO: 7 is A.

6. The plant according to claim 5, wherein the plant is a non-genetically modified plant.

7. The plant according to claim 5, wherein the plant includes a stevia plant subjected to a mutagenesis treatment and a progeny plant thereof.

8. A seed, a tissue, a dried leaf, a tissue culture or a cell of the plant according to claim 5.

9. The tissue, tissue culture or cell according to claim 8, which is selected from an embryo, a meristem cell, a pollen, a leaf, a root, a root apex, a petal, a protoplast, a leaf section and a callus.

10. A method of producing a stevia plant with high rebaudioside M content ratio, the method comprising crossing the plant according to claim 5 with a second stevia plant.

11. The method according to claim 10, wherein the second plant is a stevia plant with high rebaudioside M content ratio having at least one of the following genetic features (1) and (2), and at least one of the following genetic features (3) to (7):

(1) homozygous for the allele wherein the base at the position corresponding to position 290 of SEQ ID NO: 1 is T;
(2) homozygous for the allele wherein the base at the position corresponding to position 33 of SEQ ID NO: 2 is A;
(3) homozygous for the allele wherein the base at the position corresponding to position 44 of SEQ ID NO: 3 is T;
(4) homozygous for the allele wherein the base at the position corresponding to position 40 of SEQ ID NO: 4 is T;
(5) homozygous for the allele wherein the base at the position corresponding to position 48 of SEQ ID NO: 5 is C;
(6) homozygous for the allele wherein the portion corresponding to positions 55-72 of SEQ ID NO: 6 is deleted;
(7) homozygous for the allele wherein the base at the position corresponding to position 50 of SEQ ID NO: 7 is A.

12. A method of producing the stevia plant with high rebaudioside M content ratio according to claim 5, comprising modifying the genome of a stevia plant such that the genome has at least one of the following genetic features (1) and (2) and at least one of the following genetic features (3) to (7):

(1) homozygous for the allele wherein the base at the position corresponding to position 290 of SEQ ID NO: 1 is T;
(2) homozygous for the allele wherein the base at the position corresponding to position 33 of SEQ ID NO: 2 is A;
(3) homozygous for the allele wherein the base at the position corresponding to position 44 of SEQ ID NO: 3 is T;
(4) homozygous for the allele wherein the base at the position corresponding to position 40 of SEQ ID NO: 4 is T;
(5) homozygous for the allele wherein the base at the position corresponding to position 48 of SEQ ID NO: 5 is C;
(6) homozygous for the allele wherein the portion corresponding to positions 55-72 of SEQ ID NO: 6 is deleted;

(7) homozygous for the allele wherein the base at the position corresponding to position 50 of SEQ ID NO: 7 is A.

13. The method according to claim 12, wherein the modification of the genome is performed by a mutagenesis treatment.

14. A method of producing an extract comprising rebaudioside M at a high content ratio, comprising obtaining an extract from the plant according to claim 5, or from the seed, tissue, dried leaf, tissue culture or cell thereof.

15. A method of producing rebaudioside M, comprising:

obtaining an extract from the plant according to claim 5, or from the seed, tissue, dried leaf, tissue culture or cell thereof; and purifying rebaudioside M from the extract.

16. A method of producing a food or beverage, a sweetener composition, a flavor or a medicament, comprising:

obtaining an extract from the plant according to claim 5, or from the seed, tissue, dried leaf, tissue culture or cell thereof; and adding the extract to a raw material for the food or beverage, sweetener composition, flavor or medicament.

17. A method of producing a food or beverage, a sweetener composition, a flavor or a medicament, comprising:

obtaining an extract from the plant according to claim 5, or from the seed, tissue, dried leaf, tissue culture or cell thereof;

purifying rebaudioside M from the extract; and adding rebaudioside M to a raw material for the food or beverage, sweetener composition, flavor or medicament.

* * * * *

SEQUENCE LISTING

```
<160> NUMBER OF SEQ ID NOS: 110

<210> SEQ ID NO 1
<211> LENGTH: 326
<212> TYPE: DNA
<213> ORGANISM: Stevia rebaudiana

<400> SEQUENCE: 1

ggcagccatt gatgatgttg ttgaatgtga ttaatttgaa tgttataaag aatttggaaa     60

agaaaaagga ggggacaaag ttgatgaaat taggggagtt atgattatga tggccatggt    120
```

gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagt atgcatttat 300
tctatcatat tttctatgag aattgg 326

<210> SEQ ID NO 2
<211> LENGTH: 70
<212> TYPE: DNA
<213> ORGANISM: Stevia rebaudiana

<400> SEQUENCE: 2
tgattttgaa aggatctgac tgtatgttta taagacatag ttatgagttt gaaccccaat 60
ggctaaccct 70

<210> SEQ ID NO 3
<211> LENGTH: 383
<212> TYPE: DNA
<213> ORGANISM: Stevia rebaudiana

<400> SEQUENCE: 3
aaggttcttt atttttaaac ttatgttaat ttattgtatc ttgtagttaa tcaagagatg 60
ctctcttgga gaaattttat ggtcataaaa cctatatcaa agagatgctc tcttggtata 120
ttccatactt aaaatatcta ttttggaaaa aaagtgtagc atcttcctgc ttttagtagg 180
tgtcaatcat tattaaattt cacaaaaccg tgcaagaatc ccagtttccc tatagtttgt 240
atacgttcct gatctagtat tttacttatg tttcaaatca atccaatcat gcttgtgtcc 300
gaaaattaaa aaacaagggt attggatgcc ctgtaccact attattaact tttcagaaaa 360
acgtgtagca tgtgtacata agg 383

<210> SEQ ID NO 4
<211> LENGTH: 297
<212> TYPE: DNA
<213> ORGANISM: Stevia rebaudiana

<400> SEQUENCE: 4
taatcatcca aaccctaatc tcgccaaaca accgaatact gatccaaacc ctgaaatgag 60
cacaactctt gaacctgatc acgagaatga agagcacaaa catgttatga cacatgtaaa 120
cgatggtttt tgctacatga aaaccctaga agacgaaacc cgtttaactg taaatcttga 180
aaacacattc tttgatgaaa aacccctttc gtatccggat cttatggact tttctgcatc 240
gaaaacggac gaatacgact tctatgatga acttgaagag ctgccaatgt cttcctc 297

<210> SEQ ID NO 5
<211> LENGTH: 390
<212> TYPE: DNA
<213> ORGANISM: Stevia rebaudiana

<400> SEQUENCE: 5
cgatggtttt tgctacatga aaaccctaga agacgaaacc cgtttaactg taaatcttga 60
aaacacattc tttgatgaaa aacccctttc gtatccggat cttatggact tttctgcatc 120
gaaaacggac gaatacgact tctatgatga acttgaagag ctgccaatgt cttcctcatc 180
attcaaaagc ttcatgagaa gtaatttctt tgaggaaaga gttcttgttc aaccttattg 240
attaagaatt taagggaagc agattatata tgtaattaaa ttttggtatt tatactttga 300

-continued

```
acttaattaa taattataat aataatccca actagaggca cttagtggag attacttata    360

tataatacta attcaaggat tattgctggt                                     390


<210> SEQ ID NO 6
<211> LENGTH: 158
<212> TYPE: DNA
<213> ORGANISM: Stevia rebaudiana

<400> SEQUENCE: 6

cgcaaacacg tatactaatc acgtaacata ttttttattt ctaaattaaa attttataac     60

aatatcatac ttgaattaaa gataacataa tatttatttt tagagtgtaa cttctaaaaa    120

atatcaacct acgaaaaagt tgtacatacc atgctaaa                           158


<210> SEQ ID NO 7
<211> LENGTH: 288
<212> TYPE: DNA
<213> ORGANISM: Stevia rebaudiana

<400> SEQUENCE: 7

atacaaaaac acaacccata tggtcaaatc aacccattca tgagtaatca ggtcaaattc     60

gctatctgag ctgatgcatt caactatttg gtctcttttt aacatttatt ttttttatta    120

ttttgaatgt agaaactttg gaactactca actggtaagt tcttgaagat gtataccggt    180

catgtaaaca aaacatattg tataactccg actttttctg taacaaatgg aaaatatatt    240

gttagtggtt cagaagatca ttgtgtctac atatgggatt tacaaggg                 288


<210> SEQ ID NO 8
<211> LENGTH: 25
<212> TYPE: DNA
<213> ORGANISM: Artificial Sequence
<220> FEATURE:
<223> OTHER INFORMATION: Synthetic DNA

<400> SEQUENCE: 8

ggcagccatt gatgatgttg ttgaa                                           25


<210> SEQ ID NO 9
<211> LENGTH: 36
<212> TYPE: DNA
<213> ORGANISM: Artificial Sequence
<220> FEATURE:
<223> OTHER INFORMATION: Synthetic DNA

<400> SEQUENCE: 9

ccaattctca tagaaaatat gatagaataa atgcat                               36


<210> SEQ ID NO 10
<211> LENGTH: 32
<212> TYPE: DNA
<213> ORGANISM: Artificial Sequence
<220> FEATURE:
<223> OTHER INFORMATION: Synthetic DNA

<400> SEQUENCE: 10

tgattttgaa aggatctgac tgtatgttta ta                                   32


<210> SEQ ID NO 11
<211> LENGTH: 20
<212> TYPE: DNA
<213> ORGANISM: Artificial Sequence
<220> FEATURE:
<223> OTHER INFORMATION: Synthetic DNA
```

<400> SEQUENCE: 11
agggttagcc attggggttc 20

<210> SEQ ID NO 12
<211> LENGTH: 43
<212> TYPE: DNA
<213> ORGANISM: Artificial Sequence
<220> FEATURE:
<223> OTHER INFORMATION: Synthetic DNA

<400> SEQUENCE: 12
aaggttcttt atttttaaac ttatgttaat ttattgtatc ttg 43

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
ccttatgtac acatgctaca c 21

<210> SEQ ID NO 14
<211> LENGTH: 39
<212> TYPE: DNA
<213> ORGANISM: Artificial Sequence
<220> FEATURE:
<223> OTHER INFORMATION: Synthetic DNA

<400> SEQUENCE: 14
taatcatcca aaccctaatc tcgccaaaca accgaatac 39

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
gaggaagaca ttggcaactc 20

<210> SEQ ID NO 16
<211> LENGTH: 47
<212> TYPE: DNA
<213> ORGANISM: Artificial Sequence
<220> FEATURE:
<223> OTHER INFORMATION: Synthetic DNA

<400> SEQUENCE: 16
cgatggtttt tgctacatga aaaccctaga agacgaaacc cgtttaa 47

<210> SEQ ID NO 17
<211> LENGTH: 23
<212> TYPE: DNA
<213> ORGANISM: Artificial Sequence
<220> FEATURE:
<223> OTHER INFORMATION: Synthetic DNA

<400> SEQUENCE: 17
accagcaata atccttgaat tag 23

<210> SEQ ID NO 18

<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
cgcaaacacg tatactaatc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
tttagcatgg tatgtacaac 20

<210> SEQ ID NO 20
<211> LENGTH: 49
<212> TYPE: DNA
<213> ORGANISM: Artificial Sequence
<220> FEATURE:
<223> OTHER INFORMATION: Synthetic DNA

<400> SEQUENCE: 20
atacaaaaac acaacccata tggtcaaatc aacccattca tgagtaatc 49

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA

<400> SEQUENCE: 21
cccttgtaaa tcccatatgt ag 22

<210> SEQ ID NO 22
<211> LENGTH: 21
<212> TYPE: DNA
<213> ORGANISM: Stevia rebaudiana

<400> SEQUENCE: 22
atgcttttag tatgcattta t 21

<210> SEQ ID NO 23
<211> LENGTH: 41
<212> TYPE: DNA
<213> ORGANISM: Stevia rebaudiana

<400> SEQUENCE: 23
cccctaattt atgcttttag tatgcattta ttctatcata t 41

<210> SEQ ID NO 24
<211> LENGTH: 61
<212> TYPE: DNA
<213> ORGANISM: Stevia rebaudiana

<400> SEQUENCE: 24
gatagtgttt cccctaattt atgcttttag tatgcattta ttctatcata ttttctatga 60
g 61

<210> SEQ ID NO 25
<211> LENGTH: 21
<212> TYPE: DNA
<213> ORGANISM: Stevia rebaudiana

<400> SEQUENCE: 25
tatgtttata agacatagtt a 21

<210> SEQ ID NO 26
<211> LENGTH: 41
<212> TYPE: DNA
<213> ORGANISM: Stevia rebaudiana

<400> SEQUENCE: 26
gatctgactg tatgtttata agacatagtt atgagtttga a 41

<210> SEQ ID NO 27
<211> LENGTH: 61
<212> TYPE: DNA
<213> ORGANISM: Stevia rebaudiana

<400> SEQUENCE: 27
attttgaaag gatctgactg tatgtttata agacatagtt atgagtttga accccaatgg 60
c 61

<210> SEQ ID NO 28
<211> LENGTH: 21
<212> TYPE: DNA
<213> ORGANISM: Stevia rebaudiana

<400> SEQUENCE: 28
ttgtatcttg tagttaatca a 21

<210> SEQ ID NO 29
<211> LENGTH: 41
<212> TYPE: DNA
<213> ORGANISM: Stevia rebaudiana

<400> SEQUENCE: 29
tgttaattta ttgtatcttg tagttaatca agagatgctc t 41

<210> SEQ ID NO 30
<211> LENGTH: 61
<212> TYPE: DNA
<213> ORGANISM: Stevia rebaudiana

<400> SEQUENCE: 30
tttaaactta tgttaattta ttgtatcttg tagttaatca agagatgctc tcttggagaa 60
a 61

<210> SEQ ID NO 31
<211> LENGTH: 21
<212> TYPE: DNA
<213> ORGANISM: Stevia rebaudiana

<400> SEQUENCE: 31
aaccgaatac tgatccaaac c 21

<210> SEQ ID NO 32
<211> LENGTH: 41
<212> TYPE: DNA
<213> ORGANISM: Stevia rebaudiana

<400> SEQUENCE: 32
ctcgccaaac aaccgaatac tgatccaaac cctgaaatga g 41

<210> SEQ ID NO 33
<211> LENGTH: 61
<212> TYPE: DNA
<213> ORGANISM: Stevia rebaudiana

<400> SEQUENCE: 33
aaaccctaat ctcgccaaac aaccgaatac tgatccaaac cctgaaatga gcacaactct 60
t 61

<210> SEQ ID NO 34
<211> LENGTH: 21
<212> TYPE: DNA
<213> ORGANISM: Stevia rebaudiana

<400> SEQUENCE: 34
acccgtttaa ctgtaaatct t 21

<210> SEQ ID NO 35
<211> LENGTH: 41
<212> TYPE: DNA
<213> ORGANISM: Stevia rebaudiana

<400> SEQUENCE: 35
agaagacgaa acccgtttaa ctgtaaatct tgaaaacaca t 41

<210> SEQ ID NO 36
<211> LENGTH: 61
<212> TYPE: DNA
<213> ORGANISM: Stevia rebaudiana

<400> SEQUENCE: 36
tgaaaaccct agaagacgaa acccgtttaa ctgtaaatct tgaaaacaca ttctttgatg 60
a 61

<210> SEQ ID NO 37
<211> LENGTH: 20
<212> TYPE: DNA
<213> ORGANISM: Stevia rebaudiana

<400> SEQUENCE: 37
attaaaattt gaattaaaga 20

<210> SEQ ID NO 38
<211> LENGTH: 40
<212> TYPE: DNA
<213> ORGANISM: Stevia rebaudiana

<400> SEQUENCE: 38
ttatttctaa attaaaattt gaattaaaga taacataata 40

<210> SEQ ID NO 39
<211> LENGTH: 60
<212> TYPE: DNA
<213> ORGANISM: Stevia rebaudiana

<400> SEQUENCE: 39
aacatatttt ttatttctaa attaaaattt gaattaaaga taacataata tttattttta 60

<210> SEQ ID NO 40
<211> LENGTH: 21
<212> TYPE: DNA
<213> ORGANISM: Stevia rebaudiana

<400> SEQUENCE: 40
atgagtaatc aggtcaaatt c 21

<210> SEQ ID NO 41
<211> LENGTH: 41
<212> TYPE: DNA
<213> ORGANISM: Stevia rebaudiana

<400> SEQUENCE: 41
caacccattc atgagtaatc aggtcaaatt cgctatctga g 41

<210> SEQ ID NO 42
<211> LENGTH: 61
<212> TYPE: DNA
<213> ORGANISM: Stevia rebaudiana

<400> SEQUENCE: 42
atggtcaaat caacccattc atgagtaatc aggtcaaatt cgctatctga gctgatgcat 60
t 61

<210> SEQ ID NO 43
<211> LENGTH: 25
<212> TYPE: DNA
<213> ORGANISM: Artificial Sequence
<220> FEATURE:
<223> OTHER INFORMATION: Synthetic DNA

<400> SEQUENCE: 43
ggcagccatt gatgatgttg ttgaa 25

<210> SEQ ID NO 44
<211> LENGTH: 36
<212> TYPE: DNA
<213> ORGANISM: Artificial Sequence
<220> FEATURE:
<223> OTHER INFORMATION: Synthetic DNA

<400> SEQUENCE: 44
ccaattctca tagaaaatat gatagaataa atgcgt 36

<210> SEQ ID NO 45
<211> LENGTH: 326
<212> TYPE: DNA
<213> ORGANISM: Artificial Sequence
<220> FEATURE:
<223> OTHER INFORMATION: Synthetic DNA

<400> SEQUENCE: 45
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagt acgcatttat 300
tctatcatat tttctatgag aattgg 326

<210> SEQ ID NO 46

<211> LENGTH: 290
<212> TYPE: DNA
<213> ORGANISM: Artificial Sequence
<220> FEATURE:
<223> OTHER INFORMATION: Synthetic DNA

<400> SEQUENCE: 46

```
ggcagccatt gatgatgttg ttgaatgtga ttaatttgaa tgttataaag aatttggaaa     60

agaaaaagga ggggacaaag ttgatgaaat taggggagtt atgattatga tggccatggt    120

gattgtgatg agtggcacta tgtaatctaa tatttgaaga tatgagacca cttgaccatg    180

ttataatctt atacaaaata attaatccct cacggtaatt tttttctaat ccttaaactg    240

aaatttgaaa gtaatttgag atagtgtttc ccctaattta tgcttttagt               290
```

<210> SEQ ID NO 47
<211> LENGTH: 36
<212> TYPE: DNA
<213> ORGANISM: Artificial Sequence
<220> FEATURE:
<223> OTHER INFORMATION: Synthetic DNA

<400> SEQUENCE: 47

```
acgcatttat tctatcatat tttctatgag aattgg                               36
```

<210> SEQ ID NO 48
<211> LENGTH: 326
<212> TYPE: DNA
<213> ORGANISM: Artificial Sequence
<220> FEATURE:
<223> OTHER INFORMATION: Synthetic DNA

<400> SEQUENCE: 48

```
ggcagccatt gatgatgttg ttgaatgtga ttaatttgaa tgttataaag aatttggaaa     60

agaaaaagga ggggacaaag ttgatgaaat taggggagtt atgattatga tggccatggt    120

gattgtgatg agtggcacta tgtaatctaa tatttgaaga tatgagacca cttgaccatg    180

ttataatctt atacaaaata attaatccct cacggtaatt tttttctaat ccttaaactg    240

aaatttgaaa gtaatttgag atagtgtttc ccctaattta tgcttttagc acgcatttat    300

tctatcatat tttctatgag aattgg                                          326
```

<210> SEQ ID NO 49
<211> LENGTH: 32
<212> TYPE: DNA
<213> ORGANISM: Artificial Sequence
<220> FEATURE:
<223> OTHER INFORMATION: Synthetic DNA

<400> SEQUENCE: 49

```
tgattttgaa aggatctgac tgtatgtttt ta                                   32
```

<210> SEQ ID NO 50
<211> LENGTH: 20
<212> TYPE: DNA
<213> ORGANISM: Artificial Sequence
<220> FEATURE:
<223> OTHER INFORMATION: Synthetic DNA

<400> SEQUENCE: 50

```
tgttgaccat caagccacat                                                 20
```

<210> SEQ ID NO 51
<211> LENGTH: 196

```
<212> TYPE: DNA
<213> ORGANISM: Artificial Sequence
<220> FEATURE:
<223> OTHER INFORMATION: Synthetic DNA

<400> SEQUENCE: 51

tgattttgaa aggatctgac tgtatgtttt taagacatag ttatgagttt gaaccccaat      60

ggctaaccct tttagagaag ctccatcacc taccggtggt tcctgtcgga ttattgccac     120

cagaaaaacc caccaacatc gaagacggga atgatgagac gtgggacaca gtcaagatgt     180

ggcttgatgg tcaaca                                                     196


<210> SEQ ID NO 52
<211> LENGTH: 30
<212> TYPE: DNA
<213> ORGANISM: Artificial Sequence
<220> FEATURE:
<223> OTHER INFORMATION: Synthetic DNA

<400> SEQUENCE: 52

tgattttgaa aggatctgac tgtatgtttt                                       30


<210> SEQ ID NO 53
<211> LENGTH: 166
<212> TYPE: DNA
<213> ORGANISM: Artificial Sequence
<220> FEATURE:
<223> OTHER INFORMATION: Synthetic DNA

<400> SEQUENCE: 53

taagacatag ttatgagttt gaaccccaat ggctaaccct tttagagaag ctccatcacc      60

taccggtggt tcctgtcgga ttattgccac cagaaaaacc caccaacatc gaagacggga     120

atgatgagac gtgggacaca gtcaagatgt ggcttgatgg tcaaca                    166


<210> SEQ ID NO 54
<211> LENGTH: 196
<212> TYPE: DNA
<213> ORGANISM: Artificial Sequence
<220> FEATURE:
<223> OTHER INFORMATION: Synthetic DNA

<400> SEQUENCE: 54

tgattttgaa aggatctgac tgtatgtttt tatgacatag ttatgagttt gaaccccaat      60

ggctaaccct tttagagaag ctccatcacc taccggtggt tcctgtcgga ttattgccac     120

cagaaaaacc caccaacatc gaagacggga atgatgagac gtgggacaca gtcaagatgt     180

ggcttgatgg tcaaca                                                     196


<210> SEQ ID NO 55
<211> LENGTH: 43
<212> TYPE: DNA
<213> ORGANISM: Artificial Sequence
<220> FEATURE:
<223> OTHER INFORMATION: Synthetic DNA

<400> SEQUENCE: 55

aaggttcttt atttttaaac ttatgttaat ttattgtatc tag                        43


<210> SEQ ID NO 56
<211> LENGTH: 21
<212> TYPE: DNA
<213> ORGANISM: Artificial Sequence
<220> FEATURE:
```

<223> OTHER INFORMATION: Synthetic DNA

<400> SEQUENCE: 56
ccttatgtac acatgctaca c 21

<210> SEQ ID NO 57
<211> LENGTH: 383
<212> TYPE: DNA
<213> ORGANISM: Artificial Sequence
<220> FEATURE:
<223> OTHER INFORMATION: Synthetic DNA

<400> SEQUENCE: 57
aaggttcttt atttttaaac ttatgttaat ttattgtatc tagtagttaa tcaagagatg 60
ctctcttgga gaaattttat ggtcataaaa cctatatcaa agagatgctc tcttggtata 120
ttccatactt aaaatatcta ttttggaaaa aaagtgtagc atcttcctgc ttttagtagg 180
tgtcaatcat tattaaattt cacaaaaccg tgcaagaatc ccagtttccc tatagtttgt 240
atacgttcct gatctagtat tttacttatg tttcaaatca atccaatcat gcttgtgtcc 300
gaaaattaaa aaacaagggt attggatgcc ctgtaccact attattaact tttcagaaaa 360
acgtgtagca tgtgtacata agg 383

<210> SEQ ID NO 58
<211> LENGTH: 383
<212> TYPE: DNA
<213> ORGANISM: Artificial Sequence
<220> FEATURE:
<223> OTHER INFORMATION: Synthetic DNA

<400> SEQUENCE: 58
aaggttcttt atttttaaac ttatgttaat ttattgtatc tagaagttaa tcaagagatg 60
ctctcttgga gaaattttat ggtcataaaa cctatatcaa agagatgctc tcttggtata 120
ttccatactt aaaatatcta ttttggaaaa aaagtgtagc atcttcctgc ttttagtagg 180
tgtcaatcat tattaaattt cacaaaaccg tgcaagaatc ccagtttccc tatagtttgt 240
atacgttcct gatctagtat tttacttatg tttcaaatca gtccaatcat gcttgtgtcc 300
gaaaattaaa aaacaagggt attggatgcc ctgtaccact attattaact tttcagaaaa 360
acgtgtagca tgtgtacata agg 383

<210> SEQ ID NO 59
<211> LENGTH: 344
<212> TYPE: DNA
<213> ORGANISM: Artificial Sequence
<220> FEATURE:
<223> OTHER INFORMATION: Synthetic DNA

<400> SEQUENCE: 59
ctagaagtta atcaagagat gctctcttgg agaaatttta tggtcataaa acctatatca 60
aagagatgct ctcttggtat attccatact taaaatatct attttggaaa aaaagtgtag 120
catcttcctg cttttagtag gtgtcaatca ttattaaatt tcacaaaacc gtgcaagaat 180
cccagtttcc ctatagtttg tatacgttcc tgatctagta ttttacttat gtttcaaatc 240
agtccaatca tgcttgtgtc cgaaaattaa aaaacaaggg tattggatgc cctgtaccac 300
tattattaac ttttcagaaa aacgtgtagc atgtgtacat aagg 344

<210> SEQ ID NO 60
<211> LENGTH: 39

<212> TYPE: DNA
<213> ORGANISM: Artificial Sequence
<220> FEATURE:
<223> OTHER INFORMATION: Synthetic DNA

<400> SEQUENCE: 60
taatcatcca aaccctaatc tcgccaaaca accgggtac 39

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
gaggaagaca ttggcaactc 20

<210> SEQ ID NO 62
<211> LENGTH: 297
<212> TYPE: DNA
<213> ORGANISM: Artificial Sequence
<220> FEATURE:
<223> OTHER INFORMATION: Synthetic DNA

<400> SEQUENCE: 62
taatcatcca aaccctaatc tcgccaaaca accgggtact gatccaaacc ctgaaatgag 60
cacaactctt gaacctgatc acgagaatga agagcacaaa catgttatga cacatgtaaa 120
cgatggtttt tgctacatga aaaccctaga agacgaaacc cgtttaactg taaatcttga 180
aaacacattc tttgatgaaa aacccctttc gtatccggat cttatggact tttctgcatc 240
gaaaacggac gaatacgact tctatgatga acttgaagag ctgccaatgt cttcctc 297

<210> SEQ ID NO 63
<211> LENGTH: 297
<212> TYPE: DNA
<213> ORGANISM: Artificial Sequence
<220> FEATURE:
<223> OTHER INFORMATION: Synthetic DNA

<400> SEQUENCE: 63
taatcatcca aaccctaatc tcgccaaaca accgggtacc gatccaaacc ctgaaatgag 60
cacaactctt gaacctgatc acgagaatga agagcacaaa catgttatga cacatgtaaa 120
cgatggtttt tgctacatga aaaccctaga agacgaaacc cgtttaagtg taaatcttga 180
aaacacattc tttgatgaag aaccccttto gtatccggat cttatggact tttctgcatc 240
gaaaaaggac gaatacgact tctatgatga acttgaagag ttgccaatgt cttcctc 297

<210> SEQ ID NO 64
<211> LENGTH: 258
<212> TYPE: DNA
<213> ORGANISM: Artificial Sequence
<220> FEATURE:
<223> OTHER INFORMATION: Synthetic DNA

<400> SEQUENCE: 64
cgatccaaac cctgaaatga gcacaactct tgaacctgat cacgagaatg aagagcacaa 60
acatgttatg acacatgtaa acgatggttt ttgctacatg aaaaccctag aagacgaaac 120
ccgtttaagt gtaaatcttg aaaacacatt ctttgatgaa gaaccccttt cgtatccgga 180
tcttatggac ttttctgcat cgaaaaagga cgaatacgac ttctatgatg aacttgaaga 240
gttgccaatg tcttcctc 258

<210> SEQ ID NO 65
<211> LENGTH: 47
<212> TYPE: DNA
<213> ORGANISM: Artificial Sequence
<220> FEATURE:
<223> OTHER INFORMATION: Synthetic DNA

<400> SEQUENCE: 65
cgatggtttt tgctacatga aaaccctaga agacgaaacc cgcttaa 47

<210> SEQ ID NO 66
<211> LENGTH: 23
<212> TYPE: DNA
<213> ORGANISM: Artificial Sequence
<220> FEATURE:
<223> OTHER INFORMATION: Synthetic DNA

<400> SEQUENCE: 66
accagcaata atccttgaat tag 23

<210> SEQ ID NO 67
<211> LENGTH: 390
<212> TYPE: DNA
<213> ORGANISM: Artificial Sequence
<220> FEATURE:
<223> OTHER INFORMATION: Synthetic DNA

<400> SEQUENCE: 67
cgatggtttt tgctacatga aaaccctaga agacgaaacc cgcttaactg taaatcttga 60
aaacacattc tttgatgaaa aacccctttc gtatccggat cttatggact tttctgcatc 120
gaaaacggac gaatacgact tctatgatga acttgaagag ctgccaatgt cttcctcatc 180
attcaaaagc ttcatgagaa gtaatttctt tgaggaaaga gttcttgttc aaccttattg 240
attaagaatt taagggaagc agattatata tgtaattaaa ttttggtatt tatactttga 300
acttaattaa taattataat aataatccca actagaggca cttagtggag attacttata 360
tataatacta attcaaggat tattgctggt 390

<210> SEQ ID NO 68
<211> LENGTH: 390
<212> TYPE: DNA
<213> ORGANISM: Artificial Sequence
<220> FEATURE:
<223> OTHER INFORMATION: Synthetic DNA

<400> SEQUENCE: 68
cgatggtttt tgctacatga aaaccctaga agacgaaacc cgcttaagtg taaatcttga 60
aaacacattc tttgatgaag aacccctttc gtatccggat cttatggact tttctgcatc 120
gaaaaaggac gaatacgact tctatgatga acttgaagag ttgccaatgt cttcctcatc 180
attcaaaagc ttcatgagaa gtaatttctt tgaggaaaga gttcttgttc aaccttattg 240
attaagaatt taagggaagc agattatata tgtaattaaa ttttggtatt tatactttga 300
acttaattaa taattataat aataatccca actagaggca cttagtggag attacttata 360
tataatacta attcaaggat tattgctggt 390

<210> SEQ ID NO 69
<211> LENGTH: 347
<212> TYPE: DNA
<213> ORGANISM: Artificial Sequence
<220> FEATURE:
<223> OTHER INFORMATION: Synthetic DNA

<400> SEQUENCE: 69
ttaagtgtaa atcttgaaaa cacattcttt gatgaagaac ccctttcgta tccggatctt 60
atggactttt ctgcatcgaa aaaggacgaa tacgacttct atgatgaact tgaagagttg 120
ccaatgtctt cctcatcatt caaaagcttc atgagaagta atttctttga ggaaagagtt 180
cttgttcaac cttattgatt aagaatttaa gggaagcaga ttatatatgt aattaaattt 240
tggtatttat actttgaact taattaataa ttataataat aatcccaact agaggcactt 300
agtggagatt acttatatat aatactaatt caaggattat tgctggt 347

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA

<400> SEQUENCE: 70
cgcaaacacg tatactaatc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic DNA

<400> SEQUENCE: 71
tttagcatgg tatgtacaac 20

<210> SEQ ID NO 72
<211> LENGTH: 140
<212> TYPE: DNA
<213> ORGANISM: Artificial Sequence
<220> FEATURE:
<223> OTHER INFORMATION: Synthetic DNA

<400> SEQUENCE: 72
cgcaaacacg tatactaatc acgtaacata ttttttattt ctaaattaaa atttgaatta 60
aagataacat aatatttatt tttagagtgt aacttctaaa aaatatcaac ctacgaaaaa 120
gttgtacata ccatgctaaa 140

<210> SEQ ID NO 73
<211> LENGTH: 158
<212> TYPE: DNA
<213> ORGANISM: Artificial Sequence
<220> FEATURE:
<223> OTHER INFORMATION: Synthetic DNA

<400> SEQUENCE: 73
cgcaaacacg tatactaatc acgtaacata ttttttattt ctaaattaaa attttataac 60
aatatcatac ttgaattaaa gataacataa tatttatttt tagagtgtaa cttctaaaaa 120
atatcaacct acgaaaaagt tgtacatacc atgctaaa 158

<210> SEQ ID NO 74
<211> LENGTH: 49
<212> TYPE: DNA
<213> ORGANISM: Artificial Sequence
<220> FEATURE:

<223> OTHER INFORMATION: Synthetic DNA

<400> SEQUENCE: 74
atacaaaaac acaacccata tggtcaaatc aacccattca tgagcgatc 49

<210> SEQ ID NO 75
<211> LENGTH: 22
<212> TYPE: DNA
<213> ORGANISM: Artificial Sequence
<220> FEATURE:
<223> OTHER INFORMATION: Synthetic DNA

<400> SEQUENCE: 75
cccttgtaaa tcccatatgt ag 22

<210> SEQ ID NO 76
<211> LENGTH: 288
<212> TYPE: DNA
<213> ORGANISM: Artificial Sequence
<220> FEATURE:
<223> OTHER INFORMATION: Synthetic DNA

<400> SEQUENCE: 76
atacaaaaac acaacccata tggtcaaatc aacccattca tgagcgatca ggtcaaattc 60
gctatctgag ctgatgcatt caactatttg gtctcttttt aacatttatt tttttatta 120 ttttgaatgt agaaactttg gaactactca actggtaagt tcttgaagat gtataccggt 180
catgtaaaca aaacatattg tataactccg actttttctg taacaaatgg aaaatatatt 240
gttagtggtt cagaagatca ttgtgtctac atatgggatt tacaaggg 288

<210> SEQ ID NO 77
<211> LENGTH: 288
<212> TYPE: DNA
<213> ORGANISM: Artificial Sequence
<220> FEATURE:
<223> OTHER INFORMATION: Synthetic DNA

<400> SEQUENCE: 77
atacaaaaac acaacccata tggtcaaatc aacccattca tgagcgatcg ggtcaaattc 60
gctatctgag ctgatgcatt caactatttg gtctcttttt aacatttatt tttttatta 120 ttttgaatgt agaaactttg gaactactca actggtaagt tcttgaagat gtataccggt 180
catgtaaaca aaacatattg tataactccg actttttctg taacaaatgg aaaatatatt 240
gttagtggtt cagaagatca ttgtgtctac atatgggatt tacaaggg 288

<210> SEQ ID NO 78
<211> LENGTH: 240
<212> TYPE: DNA
<213> ORGANISM: Artificial Sequence
<220> FEATURE:
<223> OTHER INFORMATION: Synthetic DNA

<400> SEQUENCE: 78
cgggtcaaat tcgctatctg agctgatgca ttcaactatt tggtctcttt ttaacattta 60 tttttttat tattttgaat gtagaaactt tggaactact caactggtaa gttcttgaag 120
atgtataccg gtcatgtaaa caaaacatat tgtataactc cgactttttc tgtaacaaat 180
ggaaaatata ttgttagtgg ttcagaagat cattgtgtct acatatggga tttacaaggg 240

<210> SEQ ID NO 79
<211> LENGTH: 326

<212> TYPE: DNA
<213> ORGANISM: Stevia rebaudiana

<400> SEQUENCE: 79
ggcagccatt gatgatgttg ttgaatgtga ttaatttgaa tgttataaag aatttggaaa 60
agaaaaagga ggggacaaag ttgatgaaat taggggagtt atgattatga tggccatggt 120
gattgtgatg agtggcacta tgtaatctaa tatttgaaga tatgagacca cttgaccatg 180
ttataatctt atacaaaata attaatccct cacggtaatt tttttctaat ccttaaactg 240
aaatttgaaa gtaatttgag atagtgtttc ccctaattta tgcttttagc atgcatttat 300
tctatcatat tttctatgag aattgg 326

<210> SEQ ID NO 80
<211> LENGTH: 21
<212> TYPE: DNA
<213> ORGANISM: Stevia rebaudiana

<400> SEQUENCE: 80
atgcttttag catgcattta t 21

<210> SEQ ID NO 81
<211> LENGTH: 41
<212> TYPE: DNA
<213> ORGANISM: Stevia rebaudiana

<400> SEQUENCE: 81
cccctaattt atgcttttag catgcattta ttctatcata t 41

<210> SEQ ID NO 82
<211> LENGTH: 61
<212> TYPE: DNA
<213> ORGANISM: Stevia rebaudiana

<400> SEQUENCE: 82
gatagtgttt cccctaattt atgcttttag catgcattta ttctatcata ttttctatga 60
g 61

<210> SEQ ID NO 83
<211> LENGTH: 70
<212> TYPE: DNA
<213> ORGANISM: Stevia rebaudiana

<400> SEQUENCE: 83
tgattttgaa aggatctgac tgtatgttta tatgacatag ttatgagttt gaaccccaat 60
ggctaaccct 70

<210> SEQ ID NO 84
<211> LENGTH: 21
<212> TYPE: DNA
<213> ORGANISM: Stevia rebaudiana

<400> SEQUENCE: 84
tatgtttata tgacatagtt a 21

<210> SEQ ID NO 85
<211> LENGTH: 41
<212> TYPE: DNA
<213> ORGANISM: Stevia rebaudiana

<400> SEQUENCE: 85
gatctgactg tatgtttata tgacatagtt atgagtttga a 41

<210> SEQ ID NO 86
<211> LENGTH: 61
<212> TYPE: DNA
<213> ORGANISM: Stevia rebaudiana

<400> SEQUENCE: 86
attttgaaag gatctgactg tatgtttata tgacatagtt atgagtttga accccaatgg 60
c 61

<210> SEQ ID NO 87
<211> LENGTH: 383
<212> TYPE: DNA
<213> ORGANISM: Stevia rebaudiana

<400> SEQUENCE: 87
aaggttcttt atttttaaac ttatgttaat ttattgtatc ttgaagttaa tcaagagatg 60
ctctcttgga gaaattttat ggtcataaaa cctatatcaa agagatgctc tcttggtata 120
ttccatactt aaaatatcta ttttggaaaa aaagtgtagc atcttcctgc ttttagtagg 180
tgtcaatcat tattaaattt cacaaaaccg tgcaagaatc ccagtttccc tatagtttgt 240
atacgttcct gatctagtat tttacttatg tttcaaatca gtccaatcat gcttgtgtcc 300
gaaaattaaa aaacaagggt attggatgcc ctgtaccact attattaact tttcagaaaa 360
acgtgtagca tgtgtacata agg 383

<210> SEQ ID NO 88
<211> LENGTH: 21
<212> TYPE: DNA
<213> ORGANISM: Stevia rebaudiana

<400> SEQUENCE: 88
ttgtatcttg aagttaatca a 21

<210> SEQ ID NO 89
<211> LENGTH: 41
<212> TYPE: DNA
<213> ORGANISM: Stevia rebaudiana

<400> SEQUENCE: 89
tgttaattta ttgtatcttg aagttaatca agagatgctc t 41

<210> SEQ ID NO 90
<211> LENGTH: 61
<212> TYPE: DNA
<213> ORGANISM: Stevia rebaudiana

<400> SEQUENCE: 90
tttaaactta tgttaattta ttgtatcttg aagttaatca agagatgctc tcttggagaa 60
a 61

<210> SEQ ID NO 91
<211> LENGTH: 297
<212> TYPE: DNA
<213> ORGANISM: Stevia rebaudiana

<400> SEQUENCE: 91
taatcatcca aaccctaatc tcgccaaaca accgaatacc gatccaaacc ctgaaatgag 60
cacaactctt gaacctgatc acgagaatga agagcacaaa catgttatga cacatgtaaa 120

```
cgatggtttt tgctacatga aaaccctaga agacgaaacc cgtttaagtg taaatcttga    180

aaacacattc tttgatgaag aaccccttc gtatccggat cttatggact tttctgcatc    240

gaaaaaggac gaatacgact tctatgatga acttgaagag ttgccaatgt cttcctc       297


<210> SEQ ID NO 92
<211> LENGTH: 21
<212> TYPE: DNA
<213> ORGANISM: Stevia rebaudiana

<400> SEQUENCE: 92

aaccgaatac cgatccaaac c                                               21


<210> SEQ ID NO 93
<211> LENGTH: 41
<212> TYPE: DNA
<213> ORGANISM: Stevia rebaudiana

<400> SEQUENCE: 93

ctcgccaaac aaccgaatac cgatccaaac cctgaaatga g                         41


<210> SEQ ID NO 94
<211> LENGTH: 61
<212> TYPE: DNA
<213> ORGANISM: Stevia rebaudiana

<400> SEQUENCE: 94

aaaccctaat ctcgccaaac aaccgaatac cgatccaaac cctgaaatga gcacaactct     60

t                                                                     61


<210> SEQ ID NO 95
<211> LENGTH: 390
<212> TYPE: DNA
<213> ORGANISM: Stevia rebaudiana

<400> SEQUENCE: 95

cgatggtttt tgctacatga aaaccctaga agacgaaacc cgtttaagtg taaatcttga     60

aaacacattc tttgatgaag aaccccttc gtatccggat cttatggact tttctgcatc    120

gaaaaaggac gaatacgact tctatgatga acttgaagag ttgccaatgt cttcctcatc    180

attcaaaagc ttcatgagaa gtaatttctt tgaggaaaga gttcttgttc aaccttattg    240

attaagaatt taagggaagc agattatata tgtaattaaa ttttggtatt tatactttga    300

acttaattaa taattataat aataatccca actagaggca cttagtggag attacttata    360

tataatacta attcaaggat tattgctggt                                    390


<210> SEQ ID NO 96
<211> LENGTH: 21
<212> TYPE: DNA
<213> ORGANISM: Stevia rebaudiana

<400> SEQUENCE: 96

acccgtttaa gtgtaaatct t                                               21


<210> SEQ ID NO 97
<211> LENGTH: 41
<212> TYPE: DNA
<213> ORGANISM: Stevia rebaudiana

<400> SEQUENCE: 97
```

agaagacgaa acccgtttaa gtgtaaatct tgaaaacaca t 41

<210> SEQ ID NO 98
<211> LENGTH: 61
<212> TYPE: DNA
<213> ORGANISM: Stevia rebaudiana

<400> SEQUENCE: 98
tgaaaaccct agaagacgaa acccgtttaa gtgtaaatct tgaaaacaca ttctttgatg 60
a 61

<210> SEQ ID NO 99
<211> LENGTH: 140
<212> TYPE: DNA
<213> ORGANISM: Stevia rebaudiana

<400> SEQUENCE: 99
cgcaaacacg tatactaatc acgtaacata ttttttattt ctaaattaaa atttgaatta 60
aagataacat aatatttatt tttagagtgt aacttctaaa aaatatcaac ctacgaaaaa 120
gttgtacata ccatgctaaa 140

<210> SEQ ID NO 100
<211> LENGTH: 38
<212> TYPE: DNA
<213> ORGANISM: Stevia rebaudiana

<400> SEQUENCE: 100
attaaaattt tataacaata tcatacttga attaaaga 38

<210> SEQ ID NO 101
<211> LENGTH: 58
<212> TYPE: DNA
<213> ORGANISM: Stevia rebaudiana

<400> SEQUENCE: 101
ttatttctaa attaaaattt tataacaata tcatacttga attaaagata acataata 58

<210> SEQ ID NO 102
<211> LENGTH: 78
<212> TYPE: DNA
<213> ORGANISM: Stevia rebaudiana

<400> SEQUENCE: 102
aacatatttt ttatttctaa attaaaattt tataacaata tcatacttga attaaagata 60
acataatatt tattttta 78

<210> SEQ ID NO 103
<211> LENGTH: 288
<212> TYPE: DNA
<213> ORGANISM: Stevia rebaudiana

<400> SEQUENCE: 103
atacaaaaac acaacccata tggtcaaatc aacccattca tgagtaatcg ggtcaaattc 60
gctatctgag ctgatgcatt caactatttg gtctcttttt aacatttatt ttttttatta 120
ttttgaatgt agaaactttg gaactactca actggtaagt tcttgaagat gtataccggt 180
catgtaaaca aaacatattg tataactccg actttttctg taacaaatgg aaaatatatt 240
gttagtggtt cagaagatca ttgtgtctac atatgggatt tacaaggg 288

<210> SEQ ID NO 104
<211> LENGTH: 21
<212> TYPE: DNA
<213> ORGANISM: Stevia rebaudiana

<400> SEQUENCE: 104
atgagtaatc gggtcaaatt c 21

<210> SEQ ID NO 105
<211> LENGTH: 41
<212> TYPE: DNA
<213> ORGANISM: Stevia rebaudiana

<400> SEQUENCE: 105
caacccattc atgagtaatc gggtcaaatt cgctatctga g 41

<210> SEQ ID NO 106
<211> LENGTH: 61
<212> TYPE: DNA
<213> ORGANISM: Stevia rebaudiana

<400> SEQUENCE: 106
atggtcaaat caacccattc atgagtaatc gggtcaaatt cgctatctga gctgatgcat 60
t 61

<210> SEQ ID NO 107
<211> LENGTH: 36
<212> TYPE: DNA
<213> ORGANISM: Artificial Sequence
<220> FEATURE:
<223> OTHER INFORMATION: Synthetic DNA

<400> SEQUENCE: 107
ccaattctca tagaaaatat gatagaataa atgtat 36

<210> SEQ ID NO 108
<211> LENGTH: 36
<212> TYPE: DNA
<213> ORGANISM: Artificial Sequence
<220> FEATURE:
<223> OTHER INFORMATION: Synthetic DNA

<400> SEQUENCE: 108
ccaattctca tagaaaatat gatagaataa atgcaa 36

<210> SEQ ID NO 109
<211> LENGTH: 32
<212> TYPE: DNA
<213> ORGANISM: Artificial Sequence
<220> FEATURE:
<223> OTHER INFORMATION: Synthetic DNA

<400> SEQUENCE: 109
tgattttgaa aggatctgac tgtatgttta ca 32

<210> SEQ ID NO 110
<211> LENGTH: 32
<212> TYPE: DNA
<213> ORGANISM: Artificial Sequence
<220> FEATURE:
<223> OTHER INFORMATION: Synthetic DNA

<400> SEQUENCE: 110
tgattttgaa aggatctgac tgtatgttta tg 32